(12) United States Patent
Nobles et al.

(10) Patent No.: US 6,911,034 B2
(45) Date of Patent: Jun. 28, 2005

(54) SUTURING METHOD AND APPARATUS

(75) Inventors: Anthony A. Nobles, Fountain Valley, CA (US); Steven E. Decker, Anaheim, CA (US); Rod T. Peterson, Anaheim, CA (US); Chad W. Trembath, Eden Prairie, MN (US)

(73) Assignee: Sterilis, Inc., Fountain Valley, CA (US)

( * ) Notice: Subject to any disclaimer, the term of this patent is extended or adjusted under 35 U.S.C. 154(b) by 0 days.

(21) Appl. No.: 09/882,821

(22) Filed: Jun. 14, 2001

(65) Prior Publication Data

US 2002/0049453 A1 Apr. 25, 2002

Related U.S. Application Data

(60) Provisional application No. 60/211,763, filed on Jun. 14, 2000.

(51) Int. Cl.$^7$ ................................................ A61B 17/04
(52) U.S. Cl. ...................................... 606/144; 606/147
(58) Field of Search ................................ 606/139, 144, 606/145, 148, 146, 147; 112/169

(56) References Cited

U.S. PATENT DOCUMENTS

| | | | |
|---|---|---|---|
| 4,841,888 A | * | 6/1989 | Mills et al. .................. 112/169 |
| 5,320,632 A | | 6/1994 | Heidmueller |
| 5,860,991 A | | 1/1999 | Klein et al. |
| 5,868,762 A | | 2/1999 | Cragg et al. |
| 6,024,747 A | * | 2/2000 | Kontos ........................ 606/139 |
| 6,059,800 A | * | 5/2000 | Hart et al. ................... 606/139 |
| 6,117,144 A | * | 9/2000 | Nobles et al. ............... 606/139 |
| 6,245,079 B1 | * | 6/2001 | Nobles et al. ............... 606/139 |
| 6,245,080 B1 | * | 6/2001 | Levinson ..................... 606/144 |

FOREIGN PATENT DOCUMENTS

EP 0941 698 A1 3/1999

* cited by examiner

*Primary Examiner*—Danny Worrell
(74) *Attorney, Agent, or Firm*—Knobbe, Martens, Olson & Bear LLP

(57) ABSTRACT

A suturing apparatus comprises an elongated body, at least one arms movable relative to the elongated body and at least one needle movable relative to the elongated body. The arm releasably holds an end portion of a length of suture. The arm has a sharp end portion adapted to pierce an inner surface of a wall of a biological structure and pass an end portion of the suture through the inner surface. The needle is adapted to pierce the inner surface of such biological structure at a location proximal to the location where the end portion of the suture was inserted. The needle captures an end portion of the suture from the arm and draws the end portion of the suture back through the inner surface. The end of the suture is then drawn out of the biological structure by removing the elongated body.

20 Claims, 27 Drawing Sheets

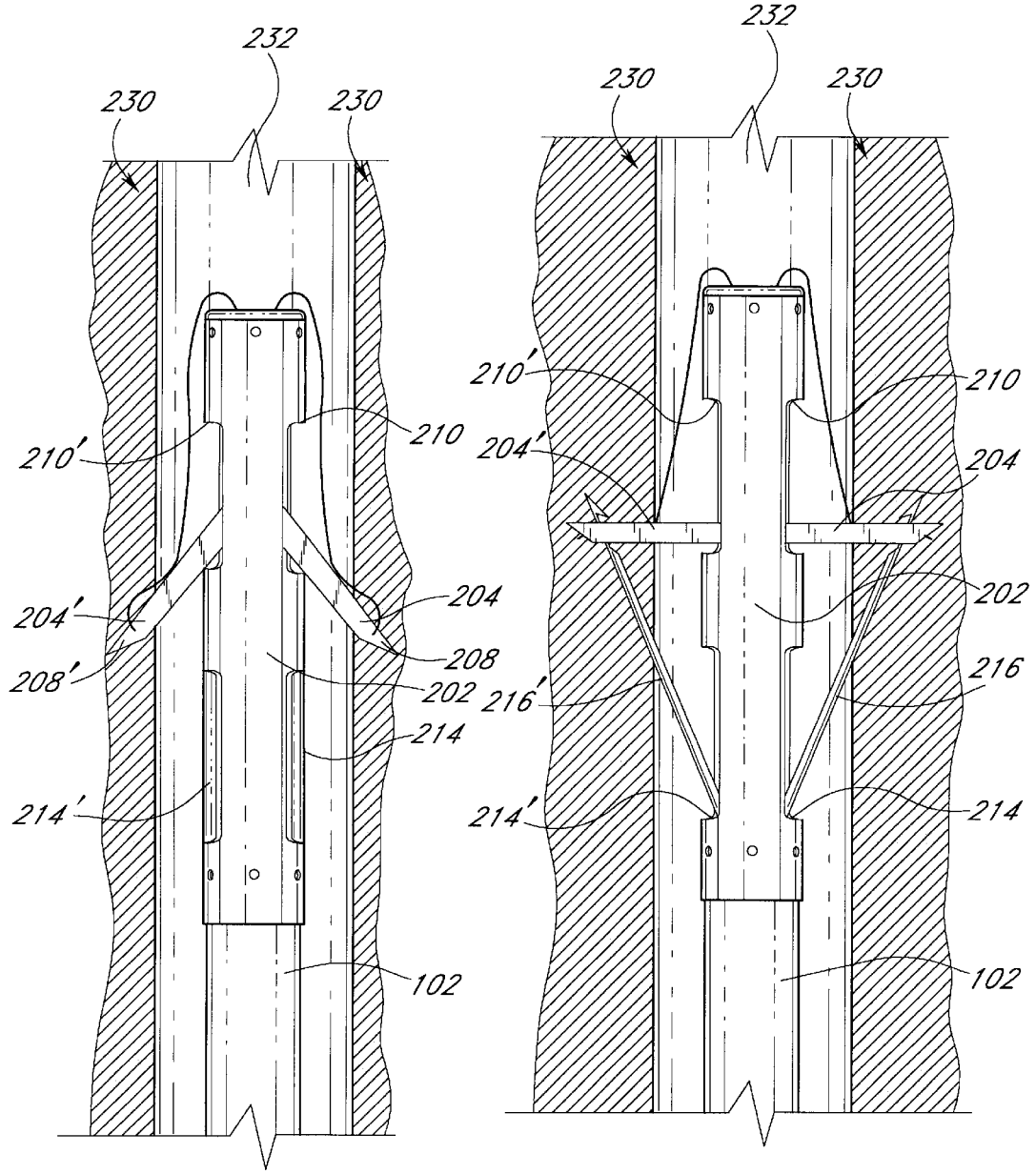

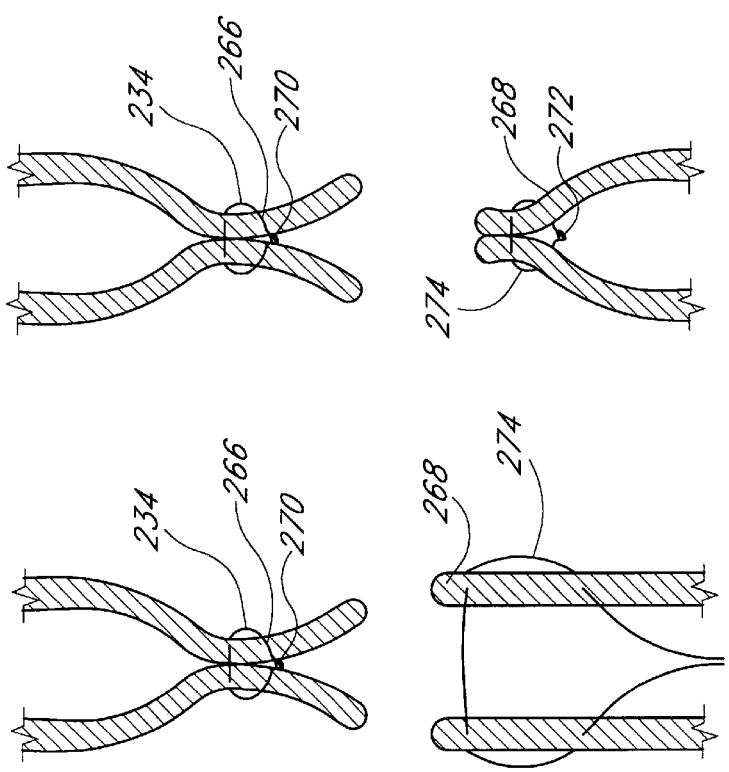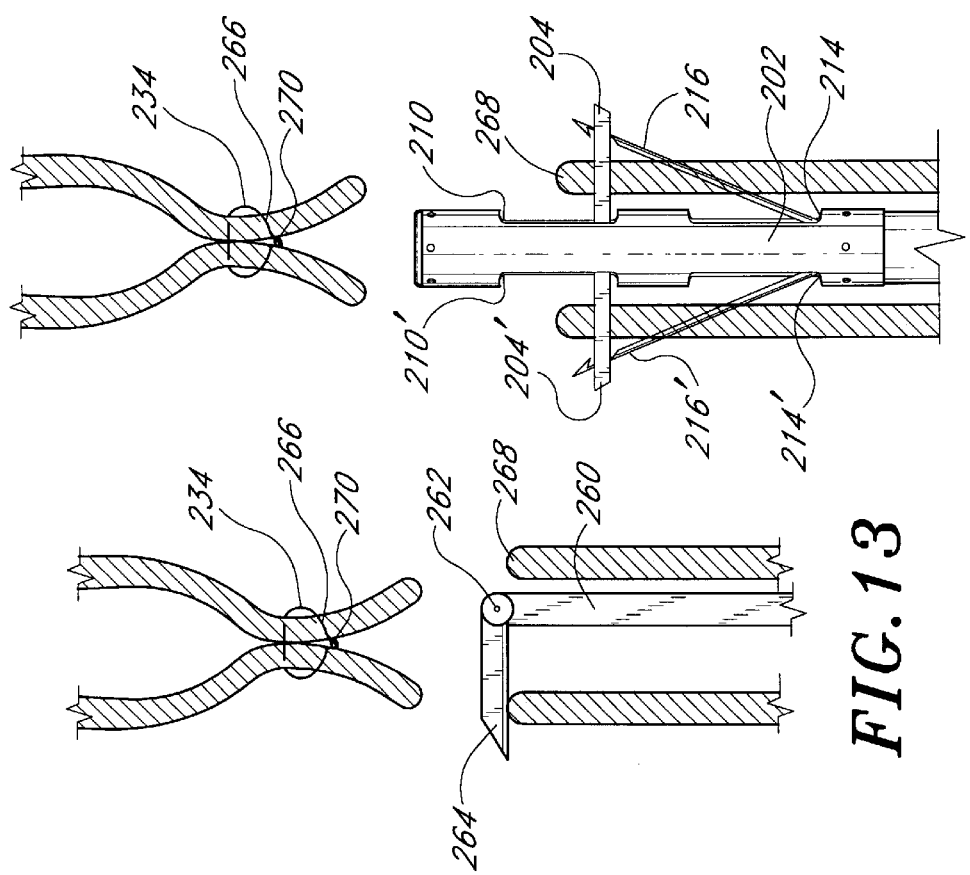
FIG. 13  FIG. 14  FIG. 15  FIG. 16

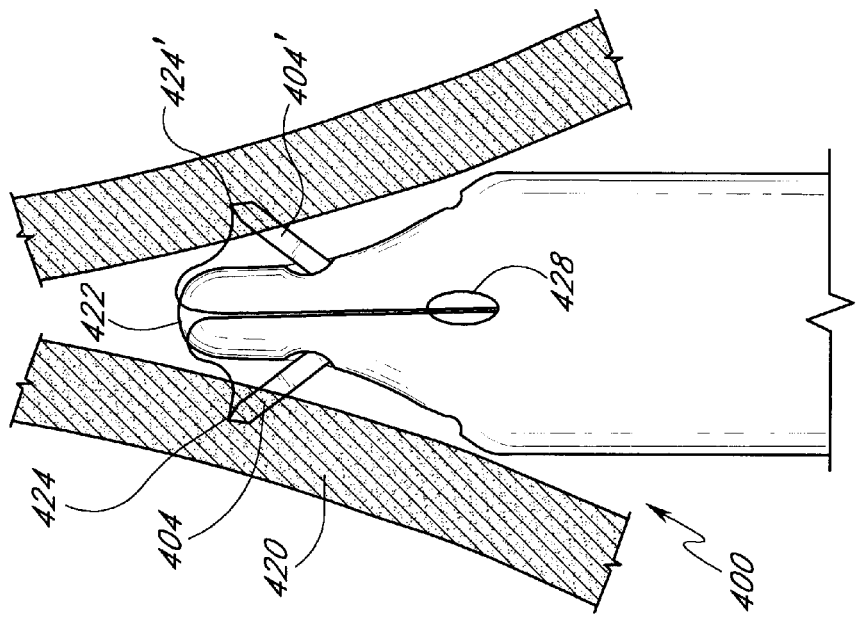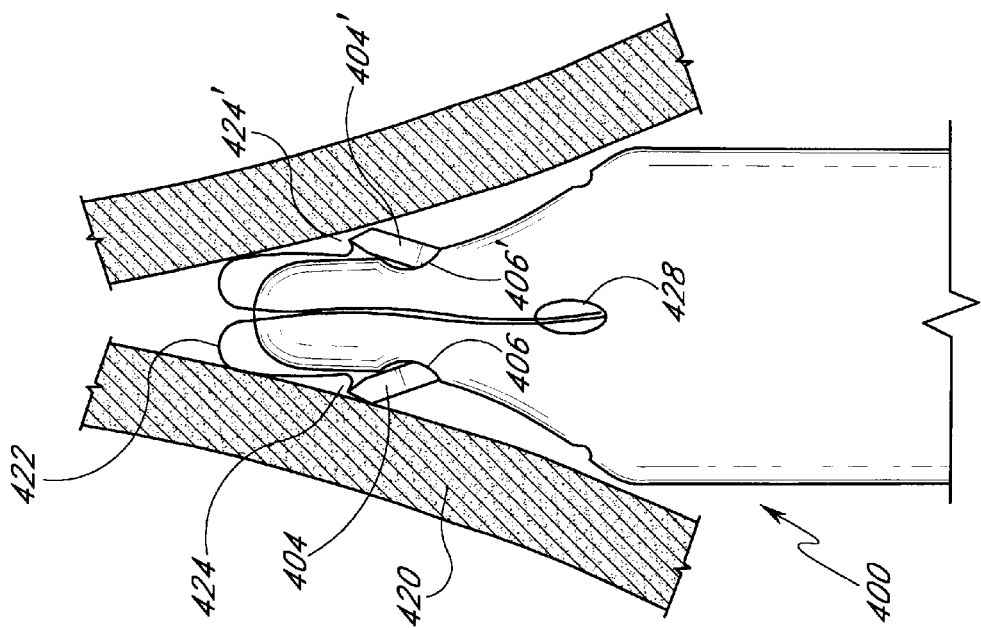

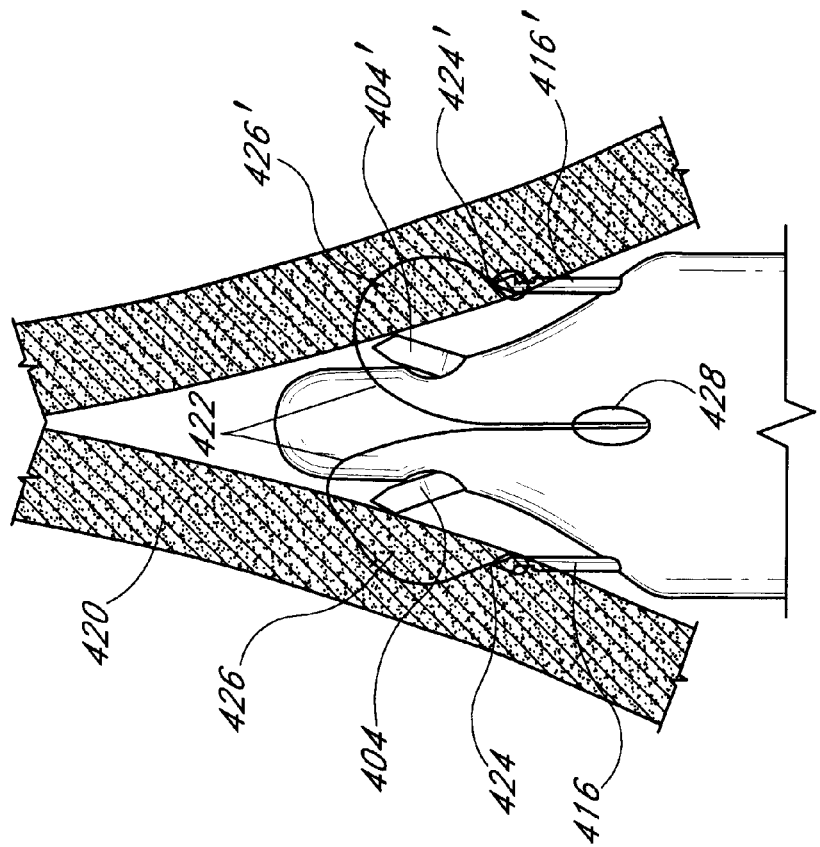
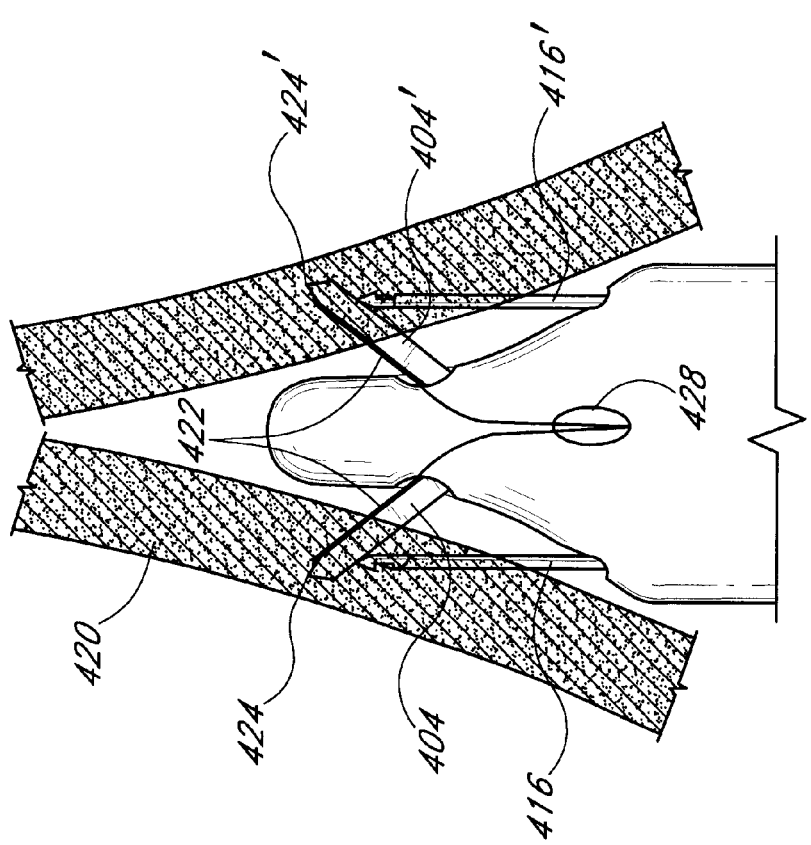

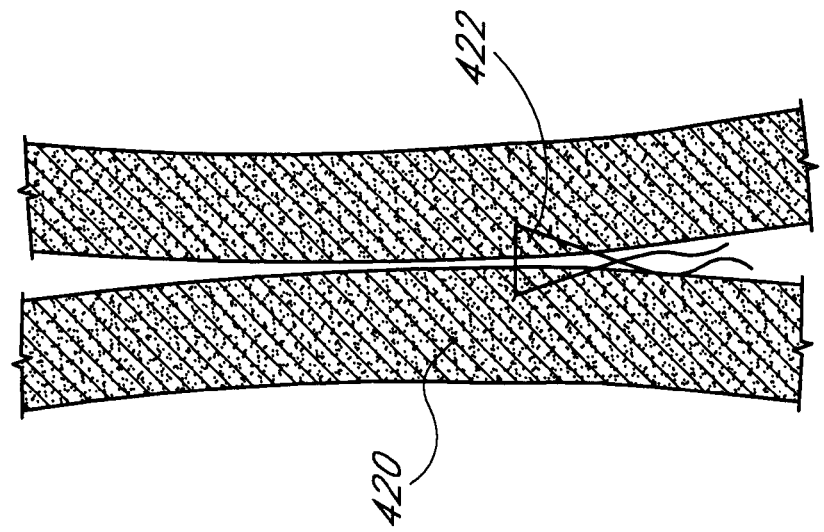
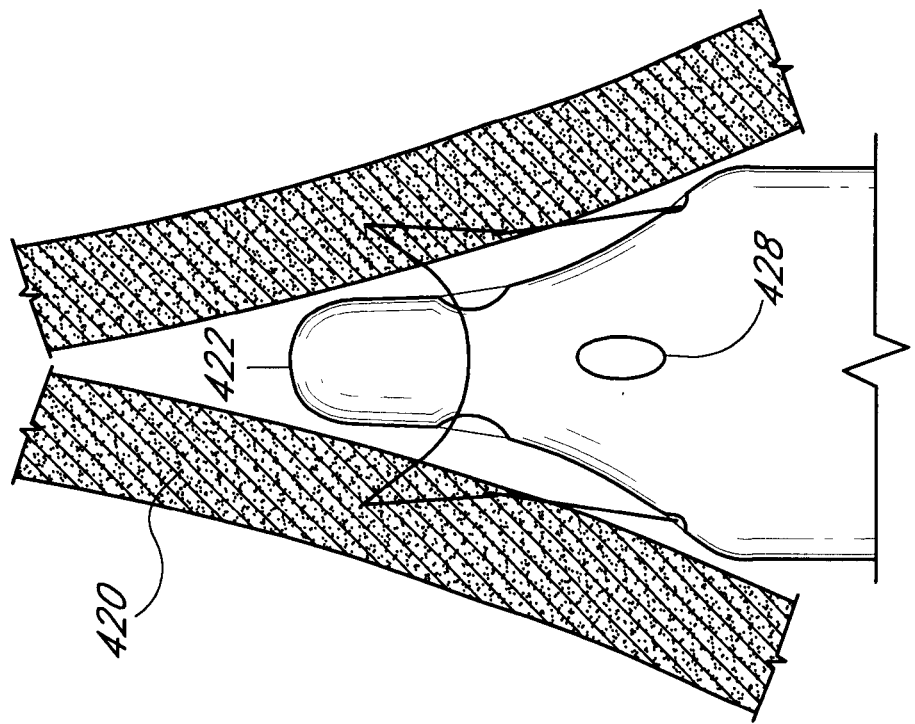

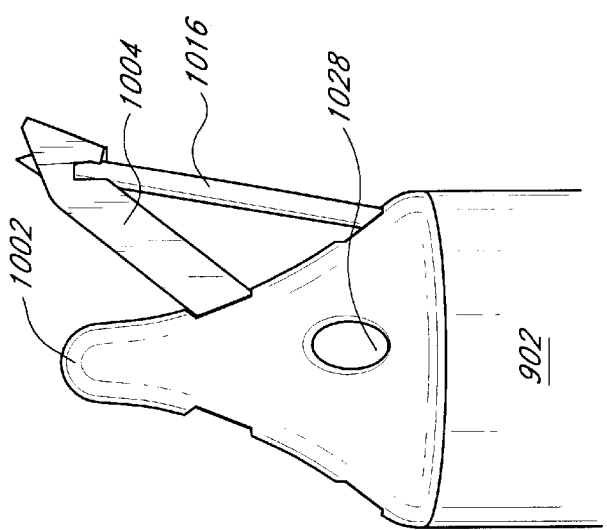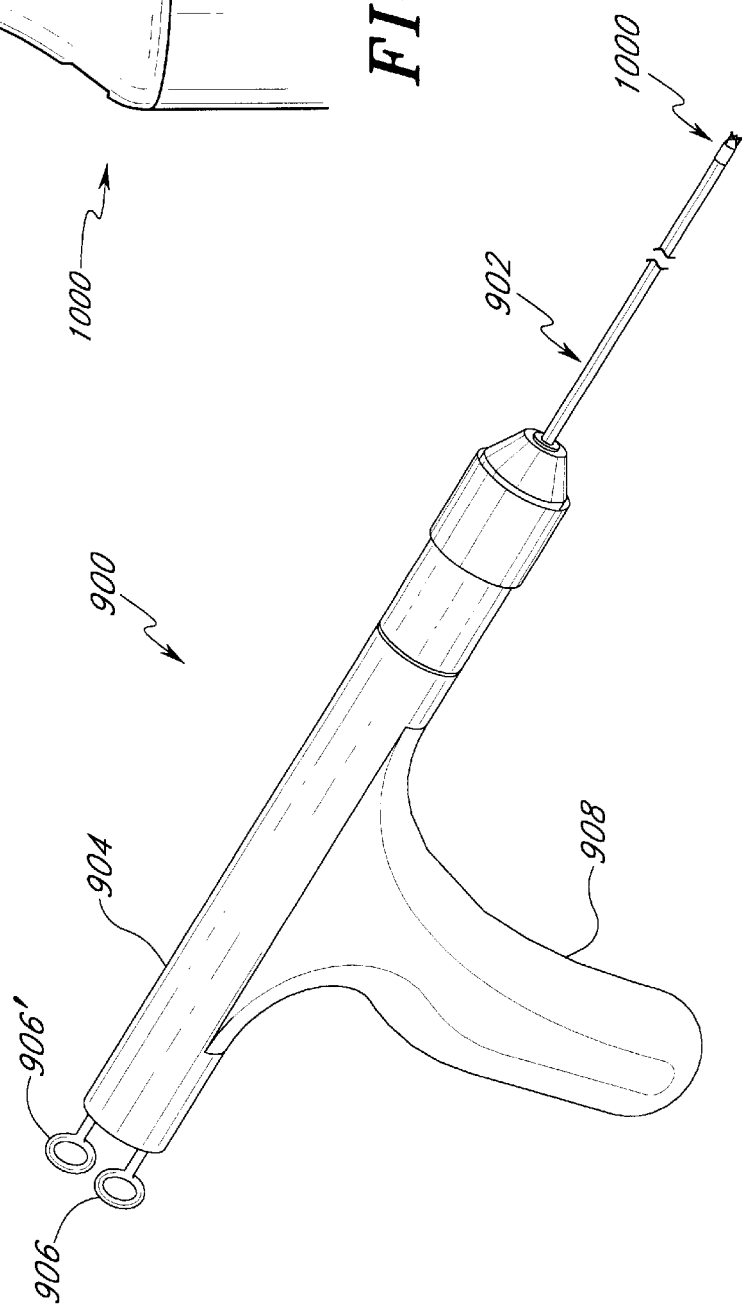

SUTURING METHOD AND APPARATUS

CROSS REFERENCE TO RELATED APPLICATION

This application claims the benefit of U.S. Provisional Application No. 60/211,763, filed Jun. 14, 2000, the entirety of which is hereby incorporated by reference.

BACKGROUND OF THE INVENTION

1. Field of the Invention

The present invention relates generally to medical devices, and more specifically to suturing devices and methods for applying suture to internal biological structures. The suturing devices and methods are well-suited for passing suture through the wall of a tubular biological structure from a location within the lumen or around the ostium for the purpose of closing the tubular biological structure. The suturing devices and methods are particularly well-suited for tubal sterilization.

2. Description of the Related Art

Each year, many thousands of women undergo some form of tubal sterilization in the United States and around the world. Tubal sterilization involves the blocking or removal of a segment from each of the fallopian tubes to prevent the fertilization of ovulated eggs. The various surgical methods used to accomplish tubal sterilization include: the laparoscopy method, the abdominal method, and the vaginal method.

In the laparoscopy method, one or two tiny incisions are made in the abdomen, in or near the navel. The laparoscope, a slim, lighted viewing tube, is inserted and a cauterizing instrument is passed through the laparoscope or through a second incision. The tubes are visualized so the surgeon can cauterize and seal each tube in turn.

In the abdominal method, a 3 to 4 inch incision is made just above the pubic hairline. The fallopian tubes are cut, sealed, and a section of each tube is removed. The ends of the tubes may be sealed or tied into the surrounding tissue.

In the vaginal method, the procedure is similar to the abdominal method. However, in this method the incision is made at the top of the vagina to avoid leaving a visible scar.

Unfortunately, these tubal sterilization procedures are quite invasive and involve the formation of one or more incisions. Because the incisions leave scars and can be damaging to the surrounding tissue, a need exists for an improved method for accomplishing tubal sterilization in a less invasive manner.

Hysterectomy is a common medical procedure in which the uterus is surgically removed from the body. Surgical removal of the uterus is widely accepted both by medical professionals and the public as an appropriate treatment for uterine cancer, and for various common non-cancerous uterine conditions that can produce often disabling levels of pain, discomfort, uterine bleeding, emotional distress, and related symptoms. A hysterectomy first requires cutting and tying the fallopian tubes to detach the uterus from the fallopian tubes. Accessing the fallopian tubes typically involves the formation of one or more incisions in the patient's skin as described above with respect to tubal sterilization procedures.

There are two traditional methods for removing the uterus from the body. The first method involves removing the uterus through a cut in the lower abdomen. The second method involves removing the uterus through a cut in the top of the vagina. The top of vagina is then sutured shut. Because these traditional hysterectomy methods involve the formation of one or more large incisions in the patient's abdomen or vagina in order to remove the uterus, a less invasive method is desired.

One less invasive method of hysterectomy has recently been developed and is known as laparoscopically-assisted vaginal hysterectomy (LAVH). In this procedure, a few small abdominal incisions are made which allow for the insertion of a laparoscope and specially designed instruments designed for detaching and removing the uterus. The procedure is referred to as "vaginal" because the uterus is then removed through the vagina. While this procedure has become quite popular with patients because of the shortened recovery time and reduced scarring, this method has been shown to have a higher complication rate than traditional vaginal or abdominal techniques. Therefore, an improved method for performing a hysterectomy is needed.

Vasectomy is a medical procedure in which the vas deferentia are surgically interrupted so that the sperm can no longer enter the ejaculatory ducts and fertilization cannot take place. In a conventional vasectomy, the surgeon makes one or two small incisions in the scrotum to gain access to the vas deferens. One vas deferens is isolated, drawn through the incision, and clamped at two sites close to each other. The segment between the clamps is then removed. The surgeon seals either one or two of the cut ends with sutures, clips, or cauterization using an electric needle. The vas deferens is gently placed back into the scrotum and the procedure is then repeated on the other vas deferens.

No-scalpel vasectomy (NSV) is a less invasive procedure in which the vas deferens are accessed without making any incisions in the scrotum. In this procedure, the surgeon makes only one tiny puncture in the scrotum using a special instrument. The instrument is then used to gently stretch the opening until the vas deferens can be pulled through it. The vas is then blocked using any of the same methods as conventional vasectomy.

A wide variety of other surgical procedures may involve the application of suture to biological structures, such as, for example, soft tissue approximation and the treatment of bladder or uterine prolapse. These procedures typically require the formation of one or more large incisions through the patient's skin in order to access the target site. Once the target site is accessed, the application of suture to the biological structure is often cumbersome and time consuming due to the anatomy of the biological structure or the consistency of the tissue.

Thus, there has been a long-felt need for new and improved devices and methods for applying suture to internal biological structures that are difficult to treat with existing suturing devices.

SUMMARY OF THE INVENTION

The preferred embodiments of the present invention describe devices and methods for applying suture to internal biological structures. The suturing devices provide means for quickly and easily applying suture to areas of the body that are often difficult to access with existing suturing devices and methods. The suturing mechanism of these devices can be operated remotely from outside the body, thereby making it possible to perform a wide variety of surgical procedures in a minimally invasive or non-invasive manner.

One aspect of the invention relates to a suturing device for closing an opening in a tubular biological structure having an inner surface, such as, for example, a fallopian tube, a common bile duct, or an arterial-venous fistula. One embodiment comprises a suturing device for applying a suture, comprising an elongated body, at least one arm having a suture mounting portion, and at least one needle having a distal end. The suture mounting portion of the arm releasably holds a portion of the suture. The arm is mounted to cause an end portion of the arm to move (i) away from the elongated body from a first position to a second position and (ii) towards the elongated body from the second position to the first position. The end portion of the arm is adapted to penetrate tissue as the arm moves away from the elongated body to the second portion while holding the portion of the suture during such movement. The needle is mounted to move relative to the elongated body, the distal end of the needle movable from a first position adjacent to the elongated body to a second position adjacent the suture mounting portion of the arm when the arm is in the second position. The distal end of the needle is adapted to capture the portion of the suture from the suture mounting portion of the arm and draws the portion of the suture toward the elongated body.

The suturing device in one preferred embodiment is particularly adapted for closing a conical or funnel-shaped biological structure such as, for example, an ostium or an infundibulum where the uterine cavity narrows into the fallopian tube. However, this embodiment is not limited to such applications, and can be used for other biological structures as well. This embodiment is formed with one or more arms that extend distally and radially at an angle ideally positioned for insertion into the tissue of the funnel-shaped biological structure. This embodiment is also well suited for soft-tissue approximation procedures and can be used to facilitate various steps in a hysterectomy procedure, as described below.

In another embodiment, the arms of the suturing device can be operated independently, thereby allowing each end portion of the suture length to be applied separately. This modification is ideally suited for closing a gap between a first body structure and a second body structure or for attaching tissue to an adjacent body structure, such as, in the treatment of bladder or uterine prolapse. This modification is also ideally suited for use in achieving male sterilization wherein the suturing device is used to loop suture around a vas deferens.

In another embodiment, the suturing device is adapted for closing wounds or surgical incisions from the surface of the skin or other biological structure. This modification includes arms that extend beyond the distal end of the elongated body for insertion into the surface from an external location. The distal end of the elongated body is placed against the surface and the arms are extended distally to penetrate the tissue on both sides of the wound. The needles are deployed to capture and withdraw the suture ends from the tissue. After the suture ends have been withdrawn, they are tied together to close the wound.

Another aspect of the present invention relates to a method of placing a suture. The method comprises positioning a distal portion of an elongated member adjacent a location to be sutured. At least one arm is deployed which releasably holds a portion of a suture. A sharp end portion of the arm penetrates tissue. A needle also penetrates tissue and is driven toward the suture portion. The suture portion is captured from the arm with the needle and drawn through the tissue and toward the elongated body.

BRIEF DESCRIPTION OF THE DRAWINGS

FIG. 7 is a side view of the distal portion of the device of FIG. 5 with the arms piercing the walls of the tubular biological structure.

FIG. 8 is a side view of the distal portion of the device of FIG. 5 with a pair of needles engaging the arms.

FIG. 13 is a partial cross-sectional view of a first suture placed in a tubular biological structure by the distal portion of the device of FIG. 1 and a cutting device severing the tubular biological structure into a distal end and a proximal end.

FIG. 14 is a partial cross-sectional view of the distal portion of the device of FIG. 1 placing a second suture in a proximal end of a severed tubular biological structure.

FIG. 15 is a partial cross-sectional view of a first suture in the distal end of the severed biological structure of FIG. 14 and a second suture in a proximal end of the severed tubular biological structure.

FIG. 16 is a partial cross-sectional view of a first securement in the first suture and a second securement in the second suture of FIG. 15.

FIGS. 20A–20F are side views of the distal portion of the device of FIG. 17 as used to apply suture to an ostium, with the ostium shown partially cut-away.

FIG. 26A is a perspective view of another embodiment of a suturing device, wherein the arms and needles of the suturing mechanism can be operated independently.

FIG. 26B is a side view of the distal portion of the device of FIG. 26A.

DETAILED DESCRIPTION OF THE PREFERRED EMBODIMENTS

The application of suture to an internal biological structure can often be difficult due to the location of the target site in the body. Therefore, a suturing procedure often requires the formation of one or more large incisions through the patient's skin simply to access the target site. Because of the highly invasive nature of such procedures and other difficulties associated with suturing internal biological structures, there is an urgent need for improved suturing devices and methods that can be used in a less invasive manner. Various forms of improved suturing devices are disclosed in U.S. Pat. No. 5,860,990 to Nobles et al., and U.S. Pat. No. 6,117,144 to Nobles et al., both of which are incorporated herein by reference in their entirety.

Figure 1:
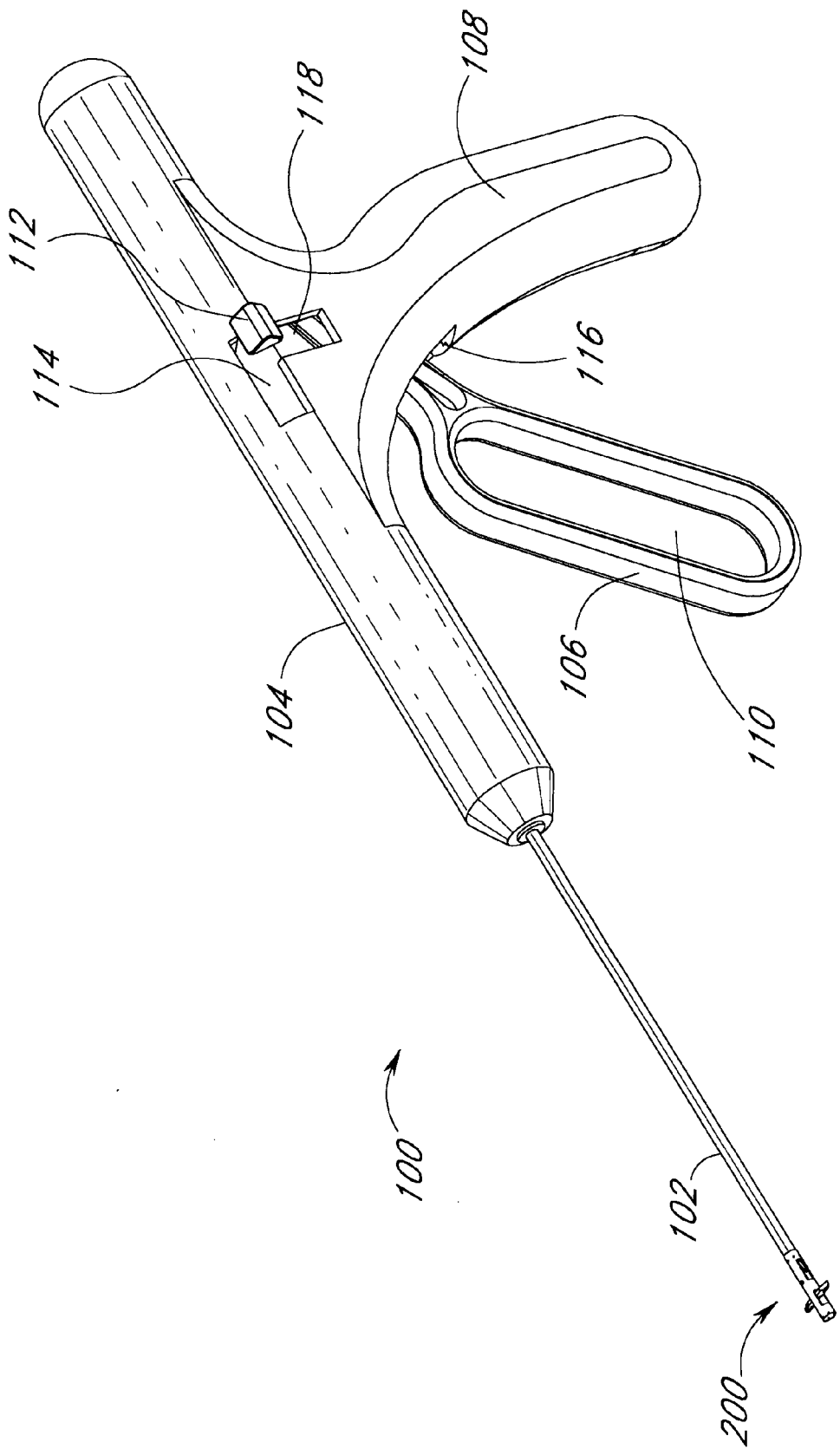
FIG. 1 is a perspective view of one embodiment of the suturing device of the present invention.

FIG. 1 illustrates a suturing device 100 in accordance with one embodiment of the present invention. The apparatus includes, generally, a shaft 102 for insertion into an internal biological structure, a main body 104, a trigger actuator 106 for actuating the suturing mechanism, and a handle 108 for gripping and manipulating the device. The shaft 102 is preferably flexible to allow it to bend when advanced through an internal biological structure, such as a body lumen. The length of the shaft 102 may be modified to accommodate various suturing applications. The trigger 106 is formed with a finger aperture 110 to ensure secure engagement with the physician's hand. A lever 112 is provided for controlling the deployment of the distal suturing components and is contained within a horizontal slot 114 and a vertical slot 118 on the handle 104. The trigger 106 and lever 112 are operatively connected to the distal portion 200 of the suturing device 100 and may be used to remotely manipulate the components of the distal portion 200.

Figure 2:
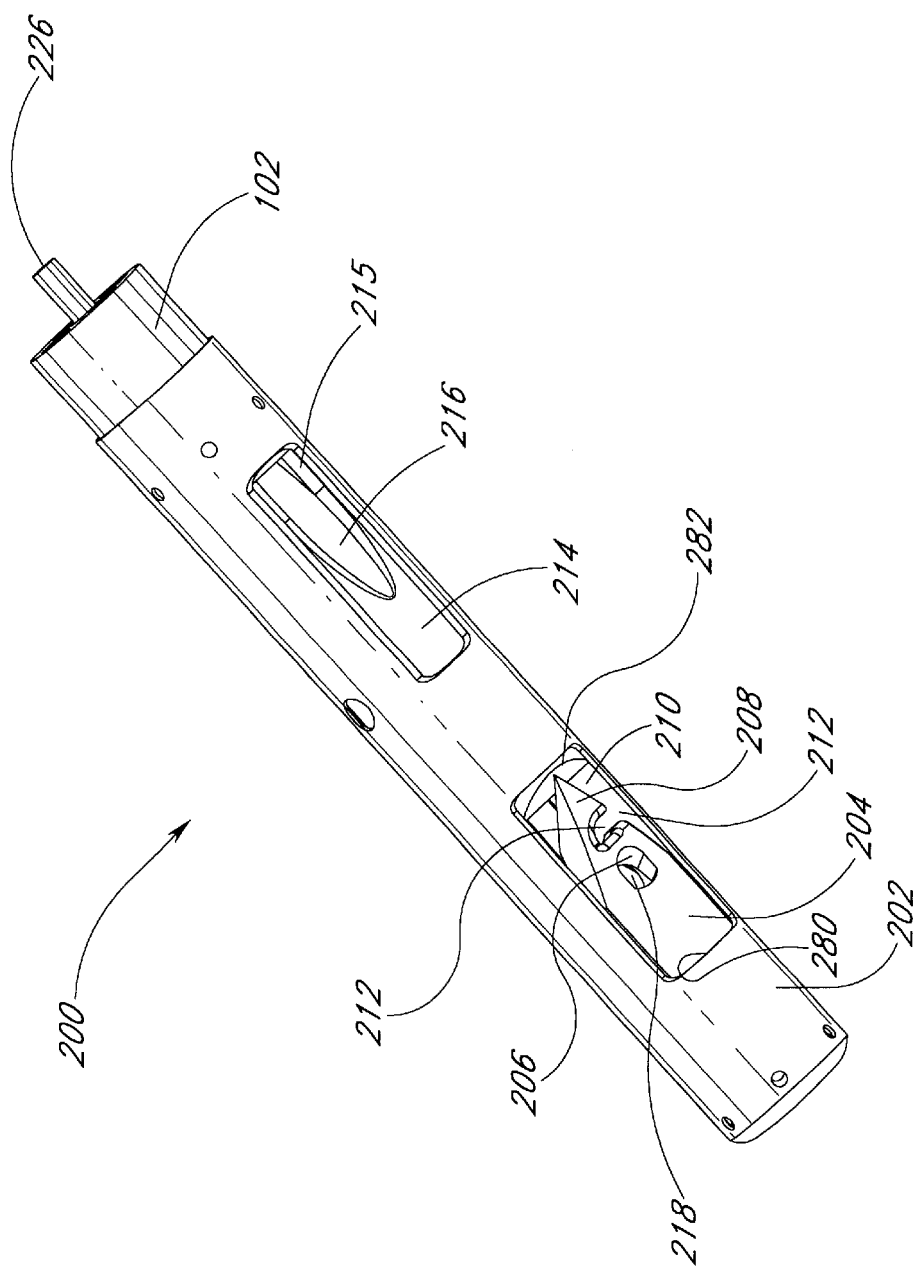
FIG. 2 is a perspective view of a distal portion of the device of FIG. 1.
Figure 3:
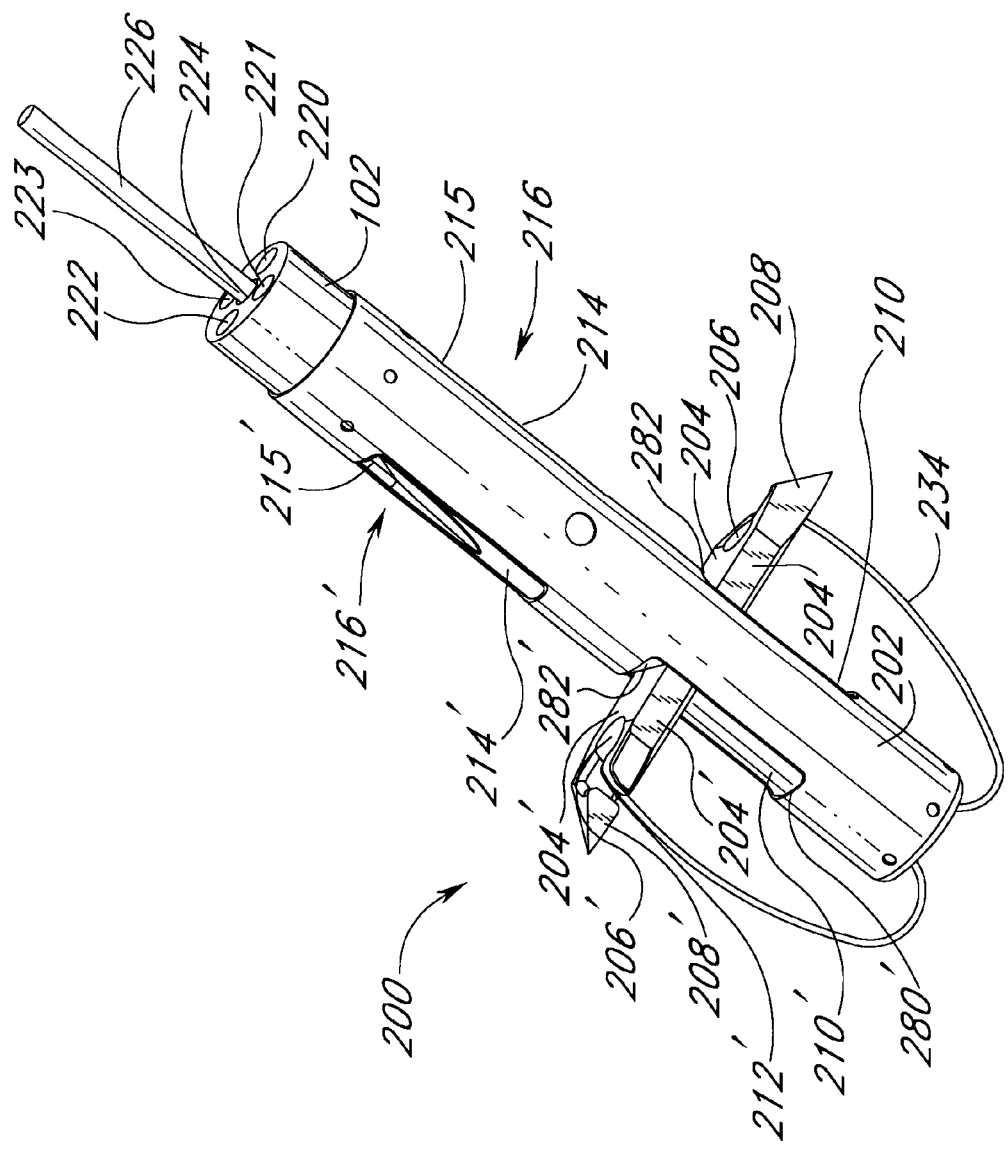
FIG. 3 is a perspective view of the distal portion of the device of FIG. 1 with a pair of arms in the deployed position.

FIGS. 2 and 3 illustrate the distal portion 200 of the device 100 in greater detail. The distal portion 200 comprises a suture introducer head 202, a pair of arms 204, 204', a pair of arm apertures 210, 210', a pair of curved or slanted upper arm guides 282, 282', a pair of lower arm guides 280, 280', a pair of needle apertures 214, 214', a pair of needles 216, 216', a pair of curved needle guides 215, 215' and an actuating rod 226. When the arms 204, 204' are retracted into the arm apertures 210, 210', the arms are recessed within the introducer head 202 so that the arms do not cause tissue damage upon insertion and retraction of the distal portion 200 from a biological structure.

FIG. 3 illustrates the distal portion 200 of the device 100 of FIG. 1 with the arms 204, 204' deployed outwardly from their recessed position. Such deployment is achieved by moving the lever actuator 112 upwardly. In FIG. 3, the shaft 102 is preferably a multi-lumen tube with a center lumen 224, two needle lumens 220, 222 and two other lumens 221, 223. The needles 216, 216' may be advanced from a recessed position within the main body 104 to a distally extended position by squeezing the trigger actuator 106. When the two needles 216, 216' are moved distally, the needle guides 215, 215' (FIG. 2) guide the needles 216, 216' out of the needle apertures 214, 214' at an angle relative to the axis of the actuating rod 226.

Figure 4:
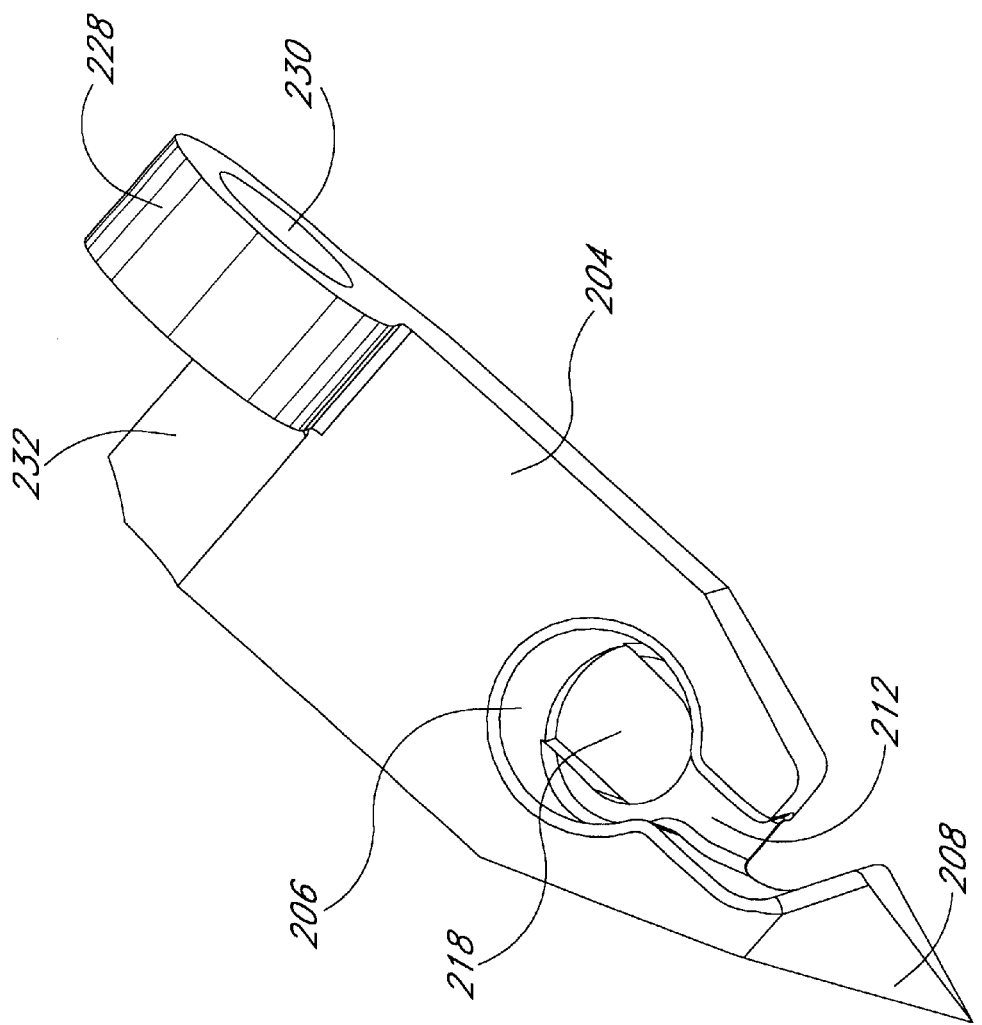
FIG. 4 is a perspective view of an arm of FIG. 3.

FIG. 4 shows details of the arm 204. The other arm 204' (FIG. 3) is identical to the arm 204 shown in FIG. 4. The arm 204 comprises a sharp end 208, a needle receiving aperture 218, a suture end support 206, a suture support 212, a hinge 228, a pin slot 230 and a hinge receiving portion 232. The hinge receiving portion 232 receives a hinge portion of the other arm 204'. Except for the configuration of the arms 204, 204', the structural components are similar to those shown and described in U.S. Pat. No. 6,117,144 and U.S. patent application Ser. No. 09/524,211, filed Mar. 13, 2000, both of which are incorporated herein by reference in their entirety. The distal end of the actuating rod 226 (the end furthest from the main body 104 of FIG. 1) is attached to the hinge portions of the arms 204, 204' via a pin (not shown). Actuation of the actuating rod 226 controls the movement of the arms 204, 204'.

Before operation, the arms 204, 204' are pre-loaded with the ends of a suture, such as a polypropylene suture. Specifically, each end of a suture has a capture portion comprised of a loop, a sphere or a ferrule. In one embodiment, the loop, sphere or ferrule may be formed (e.g., by heat molding) with the same suture material as the length of suture. In another embodiment, the loop, sphere or ferrule may be a separate piece attached (e.g., molded, glued, etc.) onto each end of the length of suture. The loop, sphere or ferrule is loaded in each suture end support 206 (FIG. 4) of the arms 204, 204'. The suture support 212 receives a portion of the suture which adjoins the loop, sphere or ferrule. The remaining length of the suture is loaded into the distal end of the introducer head 202 and into one of the lumens 221, 223 shown in FIG. 3.

When the lever actuator is moved upwardly, the actuating rod 226 translates proximally. As the actuating rod 226 translates proximally, the ends 208, 208' of the arms 204, 204' come in contact with the curved, upper arm guides 282, 282' and cause the arms 204, 204' to deploy radially. In one embodiment, the arms 204, 204' continue to deploy radially until the arms 204, 204' are substantially parallel to each other and perpendicular to the axis of the main body, as shown in FIG. 3. In other embodiments, the arms 204, 204' are considered fully deployed when they reach an acute or obtuse angle relative to each other. When the arms 204, 204' are fully deployed, either parallel to each other or at an angle, the physician may squeeze the trigger actuator 106 to move the needles 216, 216' distally. In one embodiment, the needles 216, 216' may be moved distally at substantially the same time. In another embodiment, the needles 216, 216' are actuated separately so that one needle 216 moves before the other needle 216'.

The needles 216, 216' move distally at an angle or along a curved path until the tips of the needles 216, 216' engage the capture portion of the suture ends (e.g., loop, sphere or ferrule) lying within the suture end supports 206, 206'. Such engagement causes the suture capture portions to become attached to the ends of the needles 216, 216', respectively. The physician then returns the trigger actuator to its original position to cause the needles 216, 216', with the ends of the suture attached to the ends of the needle 216, 216', to retract proximally back into the introducer head 202 and the shaft 102. The physician then moves the lever actuator such that the actuating rod 226 translates distally. As the actuating rod 226 translates distally, the arms 204, 204' come in contact with the lower arm guides 280, 280', which causes the arms 204, 204' to return to their retracted position as shown in FIG. 2. The physician then removes the distal portion 200 from the patient. As tension is applied to the suture ends, the length of the suture in the distal end of the head 202 is pulled out of the distal portion 200.

The suturing device 100 of FIG. 1 may be used to suture a variety of biological structures. In general, the physician inserts the distal portion 200 into a cavernous or tubular structure within a patient to place a suture through two tissue portions. The distal portion 200 is then withdrawn from the patient to draw the two suture ends outside of the patient. The physician ties a knot with the suture ends, slides the knot down to the suture site, and cuts the lengths of suture that are unused. One preferred method involves use of the device 100 to close a fallopian tube. Other methods may, for example, involve closing a common bile duct, or an arterial-venous fistula.

Figure 5:
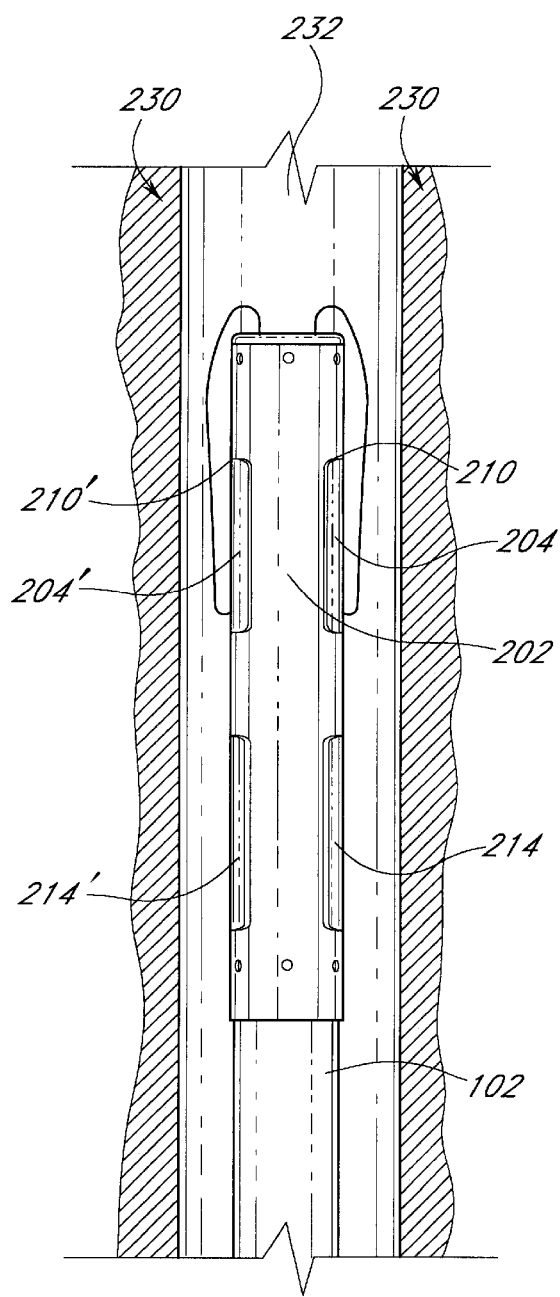
FIG. 5 is a side view of the distal portion of the device of FIG. 1 inserted in a tubular biological structure, with the tubular biological structure shown partially cutaway.

In one application, shown in FIG. 5, the physician inserts the distal portion 200, preferably with a thin sheath (not shown) covering the distal portion 200, into a patient's vagina and into a fallopian tube 232. The sheath protects the distal portion 200 from a non-sterile environment, such as the vagina. Although the shaft 102 can be inserted directly into the fallopian tube, it may be desirable to use a guidewire to guide the placement of the distal portion 200. After the guidewire is inserted into the fallopian tube, the shaft 102 is advanced along the guidewire with the guidewire within a lumen extending through the distal portion 200. The physician positions the introducer head at a desired suture location within the fallopian tube. During insertion and positioning, the arms 204, 204' are in a retracted position, with each arm 204, 204' holding one end (loop, sphere or ferrule) of a suture. The length of the suture between the end portions is stored within the introducer head 202 and/or the shaft 102 and may extend outside the handle body (104 of FIG. 1).

Figure 6:
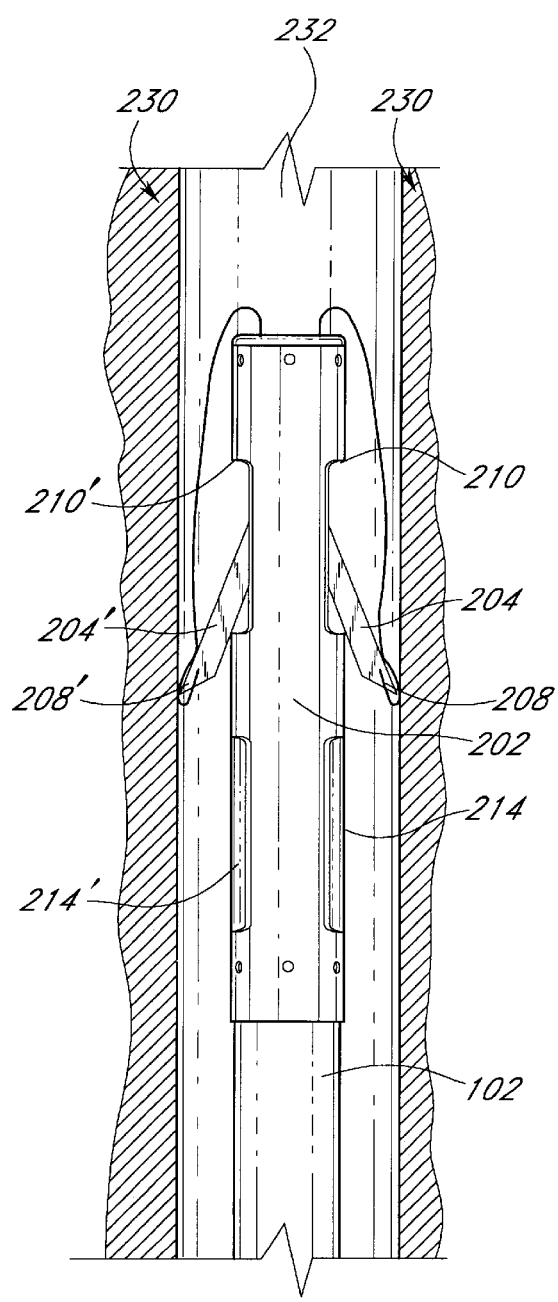
FIG. 6 is a side view of the distal portion of the device of FIG. 5 with a pair of arms opening.

Referring to FIG. 5, after the distal portion 200 is positioned at the desired location, the sheath is withdrawn to expose the arms 204, 204'. The lever 112 is then moved to actuate the arms 204, 204'. FIG. 6 illustrates the distal portion 200 with the pair of arms 204, 204' beginning to open radially outwardly.

As shown in FIG. 7, as the arms 204, 204' pivot outwardly, the sharp ends 208, 208' of the arms 204, 204' pierce the interior surface of the walls 230 of the fallopian tube 232. Additionally, although the arms 204, 204' are shown as being substantially planar with the sharp ends 208, 208' pointed in the direction of the longitudinal axis of the arms 204, 204', other configurations may be used. For example, in some situations, it may be desirable to orient the sharp ends 208, 208' at an angle relative to the longitudinal axis of the arms 204, 204' so that the sharp ends 208, 208' will be pointed more or less perpendicular to the inner surface of the walls 230 when it contacts such walls 230.

In one variation, the arms 204, 204' are deployed until the arms 204, 204' are parallel to each other as shown in FIG. 8. The length of the arms 204, 204' and/or the diameter of the introducer head 202 are selected such that the needle receiving apertures of the arms 204, 204' are well beyond the inner wall surface of the fallopian tube 232 when the arms are fully extended radially outwardly in a deployed position. Preferably, the arms 204, 204' penetrate approximately 1.0 mm into the walls 230 of the biological structure 232 on each side of the distal portion 200. However, the depth of penetration may be varied without departing from the spirit of the invention.

As shown in FIG. 8, after the arms have been extended to pierce the fallopian tube, the trigger 106 is moved to advance the needles 216, 216' towards the needle receiving portions of the arms. As the needles 216, 216' are advanced, they pierce the walls 230 of the fallopian tube 232 at a location proximal to the location where the arms 204, 204' pierced the walls 230. The needles 216, 216' continue to advance through tissue until they engage the capture portion (e.g., loops, spheres or ferrules) at the ends of the suture held by the arms 204, 204', as described above.

Figures 9, 10:
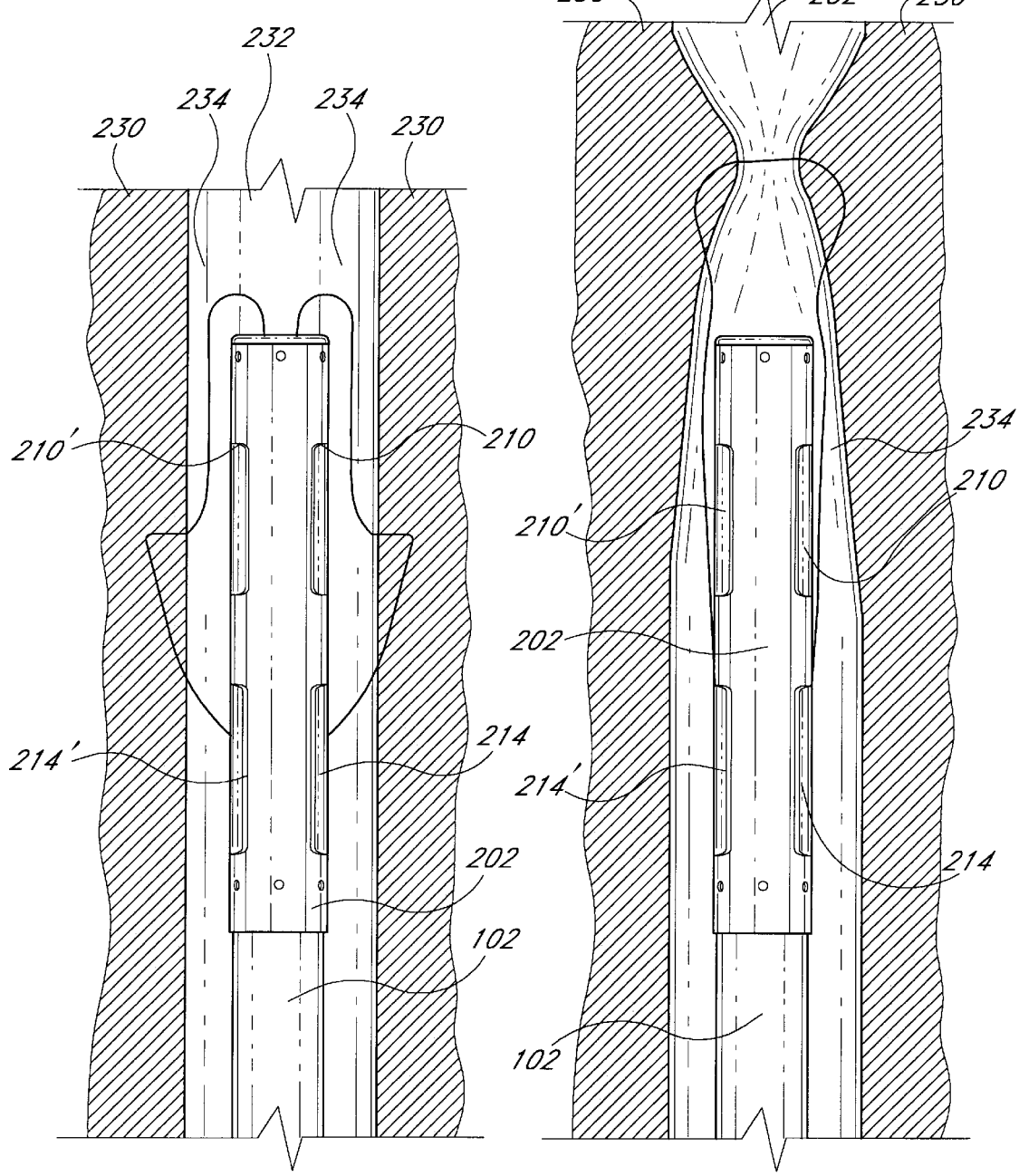
FIG. 9 is a side view of the distal portion of the device of FIG. 5 with a suture placed in the walls of the tubular biological structure by the arms and needles of the distal portion of the device of FIG. 1.
FIG. 10 is a side view of the distal portion of the device of FIG. 5, the suture of FIG. 9 pulling the walls of the tubular biological structure together.

When the needles 216, 216' are withdrawn back into the introducer head 202, the ends of the suture are also drawn into the distal portion 200, as shown in FIG. 9. The suture 234 thus passes through opposing sides of the walls 230 of the fallopian tube 232 with the ends of the suture captured by the needles 216, 216'. In FIG. 9, the physician has retracted both the needles 216, 216' and the arms 204, 204'. The physician removes the distal portion 200 from the patient, and the length of suture 234 between the end portions is released from the distal end of the introducer head 202. Once the distal portion 200 is outside the patient, the physician detaches the ends of the suture 234 from the distal portion 200.

FIG. 10 illustrates tension being applied to the suture 234 during withdrawal of the distal portion 200. Such tension pulls the walls 230 of the fallopian tube 232 inwardly. Such pulling also causes the fallopian tube 232 to constrict longitudinally. After the distal portion 200 is removed from the patient and the suture end portions detached therefrom, the physician forms a self-cinching knot, such as a clinch knot or a half hitch, with the suture end portions that extend outside of the patient and slides the knot down the fallopian tube to the suture site. The knots may be advanced to the suture site using, for example, any of the devices disclosed in co-pending U.S. application Ser. No. 09/571,759, filed May 15, 2000, which is incorporated herein by reference in its entirety. As the knot reaches the suture site, it will apply tension to the portion of the suture extending through the walls 230 and draws the walls together as well as longitudinally shorten the fallopian tube. Additional self-cinching knots may be pushed down on top of the first knot to lock the first knot in place, and the lengths of the suture 234 extending from the knot are cut by the physician. The suture 234 is preferably made of a biocompatible material.

Figure 11:
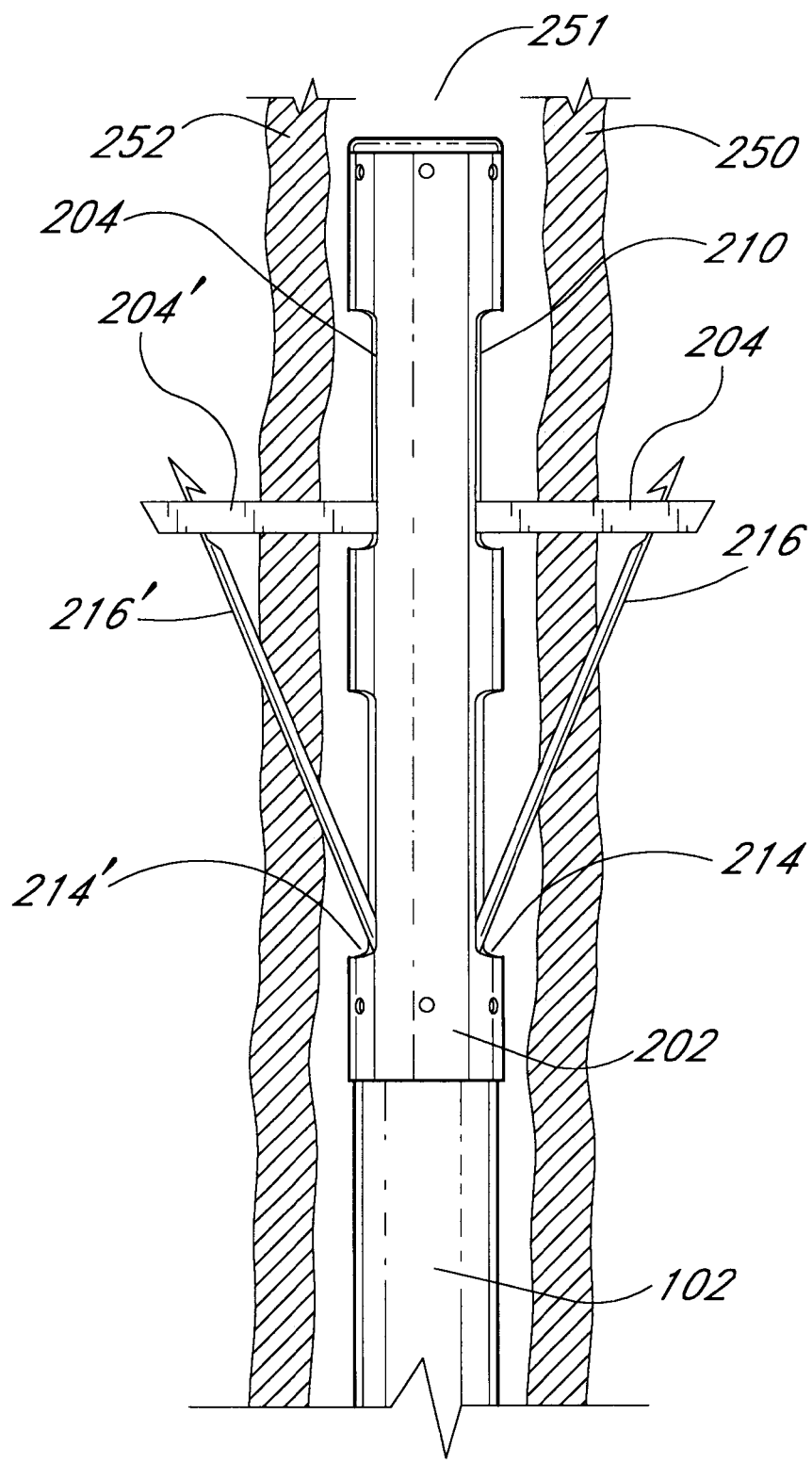
FIG. 11 is a side view of the distal portion of the device of FIG. 1, with a pair of needles engaging a pair of arms beyond the walls of a tubular biological structure shown partially cut-away.

Although the above-discussed procedure passed the suture through walls of the fallopian tube without penetrating the exterior surface of the fallopian tube, it will be understood that the suturing device 200 may also be configured to pass the suture completely through the walls so as to penetrate the exterior surface of the fallopian tube. FIG. 11 illustrates the distal portion 200 of the device 100 of FIG. 1 with both the needles 216, 216' and the arms 204, 204' extending through exterior surface of the walls 250, 252 of a tubular biological structure 251, such as a fallopian tube. The arms 204, 204' fold outwardly and puncture the walls 250, 252 such that the capture portion of the suture is exterior to the tube 251. As the unfolding arms engage the tissue to begin such penetration, the physician preferably pulls the distal portion 200 proximally to cause the pointed ends of the arms to be driven into the tissue and through the walls 250, 252. The needles 216, 216' pass through the tissue at a location proximal to the arms 204, 204' and engage the capture portions of the suture that are within the suture end supports 206, 206'. The physician then withdraws the needles 216, 216' and the ends of the suture 234 into the introducer head 202, retracts the arms 204, 204', and removes the introducer head 202 from the patient. The physician then secures the suture 234 with a securement, such as a knot, as described above with reference to FIGS. 9 and 10.

Figure 12:
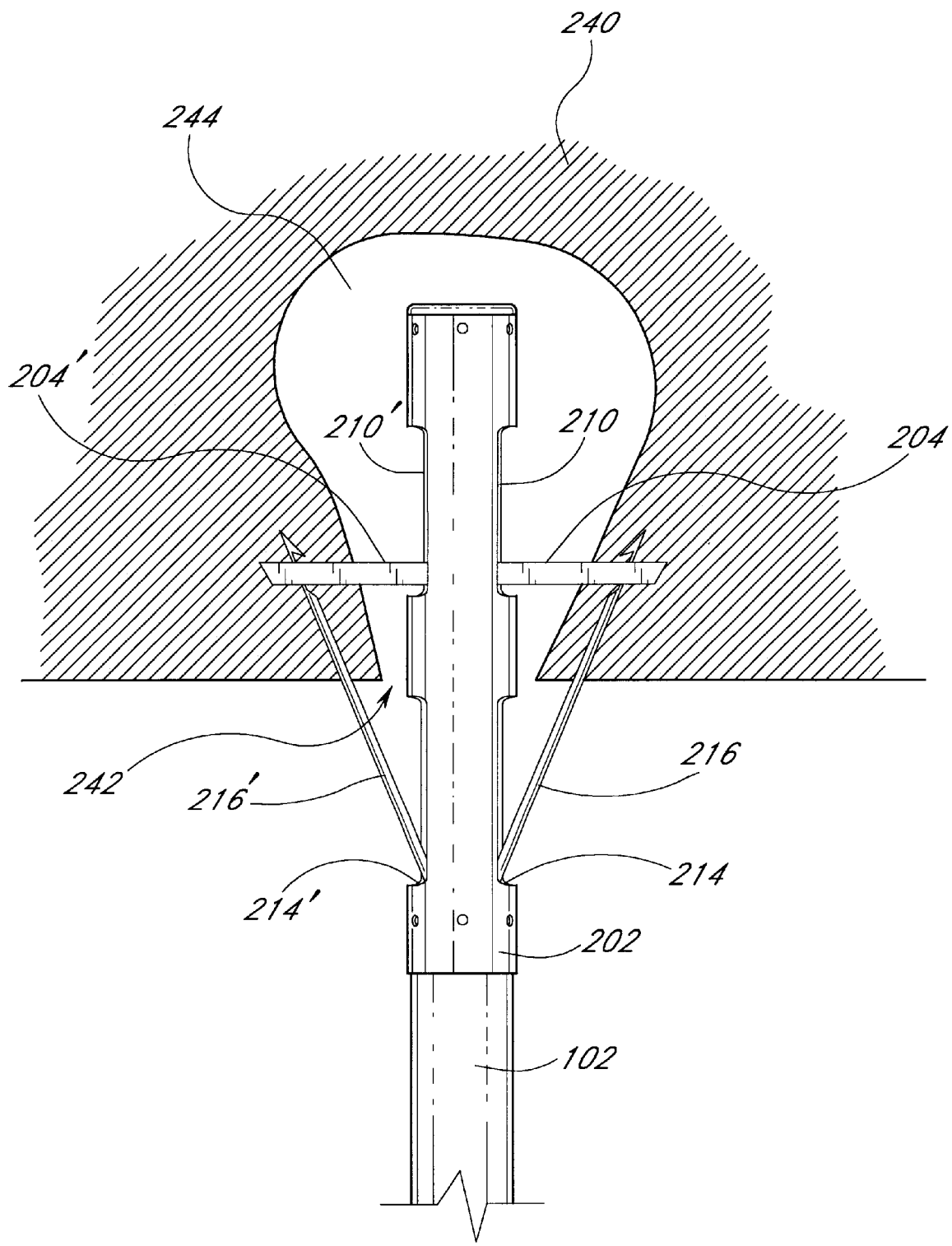
FIG. 12 is a side view of the distal portion of the device of FIG. 1 with a pair of needles engaging a pair of arms in the walls surrounding a rupture or tear of a biological structure, shown partially cut-away.

FIG. 12 illustrates the distal portion 200 of the device 100 of FIG. 1 with the needles 216, 216' engaging the arms 204, 204' in the walls of another type of biological structure 240. In FIG. 12, the distal portion 200 is used to close a suture site 242, such as an incision, rupture or tear, within the biological structure 240. For example, the rupture or tear can be an aneurysm. In operation, the physician inserts the introducer head 202 into a cavity 244 and deploys the arms 204, 204'. The physician manipulates the arms 204, 204' to pierce the walls of the structure 240. The physician then moves the needles 216, 216' distally until they engage the arms 204, 204' in the walls of the biological structure 240. The physician retracts the needles 216, 216' and the suture ends into the introducer head 202. The physician removes the introducer head 202 from the suture site and then removes the ends of the suture from the introducer head 202. The physician secures the suture with a securement such as a knot or clip. The physician then cuts the remaining, unused ends of the suture.

FIGS. 13–16 illustrate a method of using the device 100 of FIG. 1 to suture a tubular structure, such as a fallopian tube, at proximal and distal locations that are spaced from each other. In reference to FIG. 13, the physician initially uses the distal portion 200 to place a first suture 234 in the tubular structure as described above with reference to FIG. 11. The physician removes the introducer head 202 from the tubular structure, pulls the suture ends taut, and secures the first suture 234 with a first knot 270 or clip near the first suture site. The physician cuts and removes the remaining, unused ends of the suture 234.

As illustrated in FIG. 13, the physician then inserts a shaft 260 into the tubular biological structure. Preferably, the shaft 260 is flexible or bendable such that the physician can insert and position the shaft 260 at a desired location within the tubular structure. A cutter 264 is attached to the distal end of the shaft 260 by a pivot pin 262. In another embodiment, the cutter 264 and the shaft 260 are integrated as a single piece. In one embodiment, more than one cutter may be attached to the shaft 260 by one or more pivot pins. In one embodiment, the cutter is a fan-shaped blade.

During insertion of the shaft 260 into the tubular biological structure, the cutter 264 retracted. Once the shaft 260 and cutter 264 are positioned at a desired location near the first suture knot 270, the physician deploys the cutter 264. In one embodiment, the cutter 264 may be attached to an actuating rod or a spring that is attached to a lever or actuating rod at the proximal end of the shaft 260 outside of the tubular structure. The physician deploys the cutter 264 by pushing or pulling the lever or actuating rod outside of the tubular biological structure.

When the cutter 264 is deployed, the cutter 264 pierces the walls of the tubular biological structure. The physician rotates the cutter 264 to completely sever the tubular structure and thereby create a distal end 266 and a proximal end 268. The physician then retracts the cutter 264 and removes the shaft 260.

As shown in FIGS. 14–15, the physician then inserts the distal portion 200 of the device 100 of FIG. 1 (either the same device 100 loaded with another suture or another pre-loaded device 100) into the tubular structure and advances the portion 200 to a position near the second end 268. In one embodiment, a flexible, hollow tube with an inflation lumen and an inflatable balloon is inserted over the shaft 102. The physician causes the balloon to inflate and come in contact with the inner walls of the second end 268 of the severed tubular biological structure. Thus, the inflated balloon supports the second end 268 of the severed tubular biological structure as the distal portion 200 of the device 100 is used to place a second suture 274.

After the suture 274 has been passed through the tissue at the end 268, the physician removes the introducer head 202 from the tubular structure, pulls the second suture ends taut, and secures the second suture 274 with a second knot 272 or clip, as illustrated in FIGS. 15–16. The physician cuts and removes the remaining, unused ends of the suture 274.

The order of the acts described above with reference to FIGS. 13–16 may be rearranged in other embodiments of the suture method. For example, in one embodiment, the physician places the first suture 234 in the tubular biological structure, pulls the first suture 234 taut, forms a first securement 270 with ends of the first suture 234, cuts the remaining, unused ends of the first suture 234, places the second suture 274 but does not form a securement yet, inserts the flexible, hollow tube with the balloon, inflates the balloon for support, inserts the cutter 264 to cut the tubular biological structure into a first end 266 and a second end 268, pulls the second suture 274 taut, forms a second securement 272 with ends of the second suture 274 and finally cuts the remaining, unused ends of the second suture 274.

It will also be appreciated that the suturing device described in FIGS. 1–4 may incorporate more or less than two arms and needles in order to close the fallopian tube or other biological structure. Suturing devices with multiple arms and needles are described below and in U.S. Pat. No. 6,117,144 and U.S. patent application Ser. No. 09/524,211, filed Mar. 13, 2000, referenced above. By providing more than two arms and two needles around the circumference of the shaft 102, suture can be applied to more effectively close the body lumen.

Figure 17:
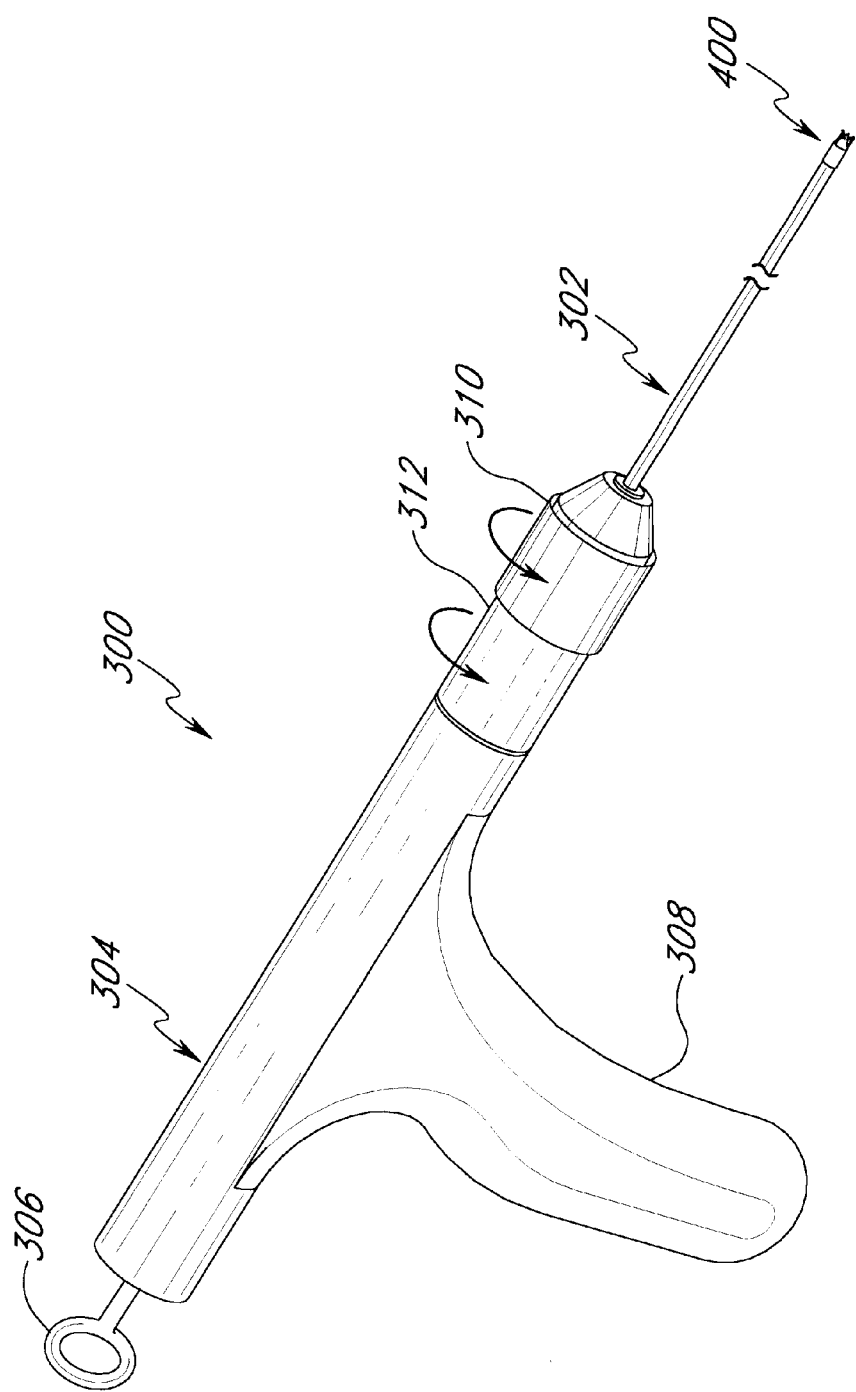
FIG. 17 is a perspective view of a second preferred embodiment of the suturing device of the present invention.

FIG. 17 illustrates a suturing device 300 in accordance with a second preferred embodiment of the present invention. One preferred use of this embodiment is to close an infundibulum, particularly the conical or funnel-shaped cavity where the uterine cavity narrows into the fallopian tube. Other uses of this embodiment include soft tissue approximation in general surgical applications (such as laparoscopy), post-hysterectomy closure of a vagina (e.g., vaginal closure at the junction between the vagina and the uterus/cervix), treatment of prolapse by attachment of a bladder or uterus to an adjacent or distant body structure, closure of blood vessels, and closure of wounds or surgical incisions in the skin.

Still referring to FIG. 17, the suturing device 300 includes, generally, an elongated shaft 302 for insertion into an internal biological structure, a main body 304, a plunger 306 and a handle 308 for gripping the suturing device. The plunger 306 is located at the proximal end of the main body 304 and is operatively connected to the distal portion 400 of the suturing device 300. Actuation of the plunger provides a means for remotely manipulating the suturing components, as described below. The suturing device includes a distal annular mechanism 310 that can be turned to articulate or bend the distal end of the elongated shaft. Furthermore, the suturing device also includes a proximal annular mechanism 312 that can be turned to rotate the entire elongated shaft. The articulation and rotation of the elongated shaft are advantageous for advancing the device through or around biological structures, and for placement of the device in difficult to reach locations.

Figure 18:
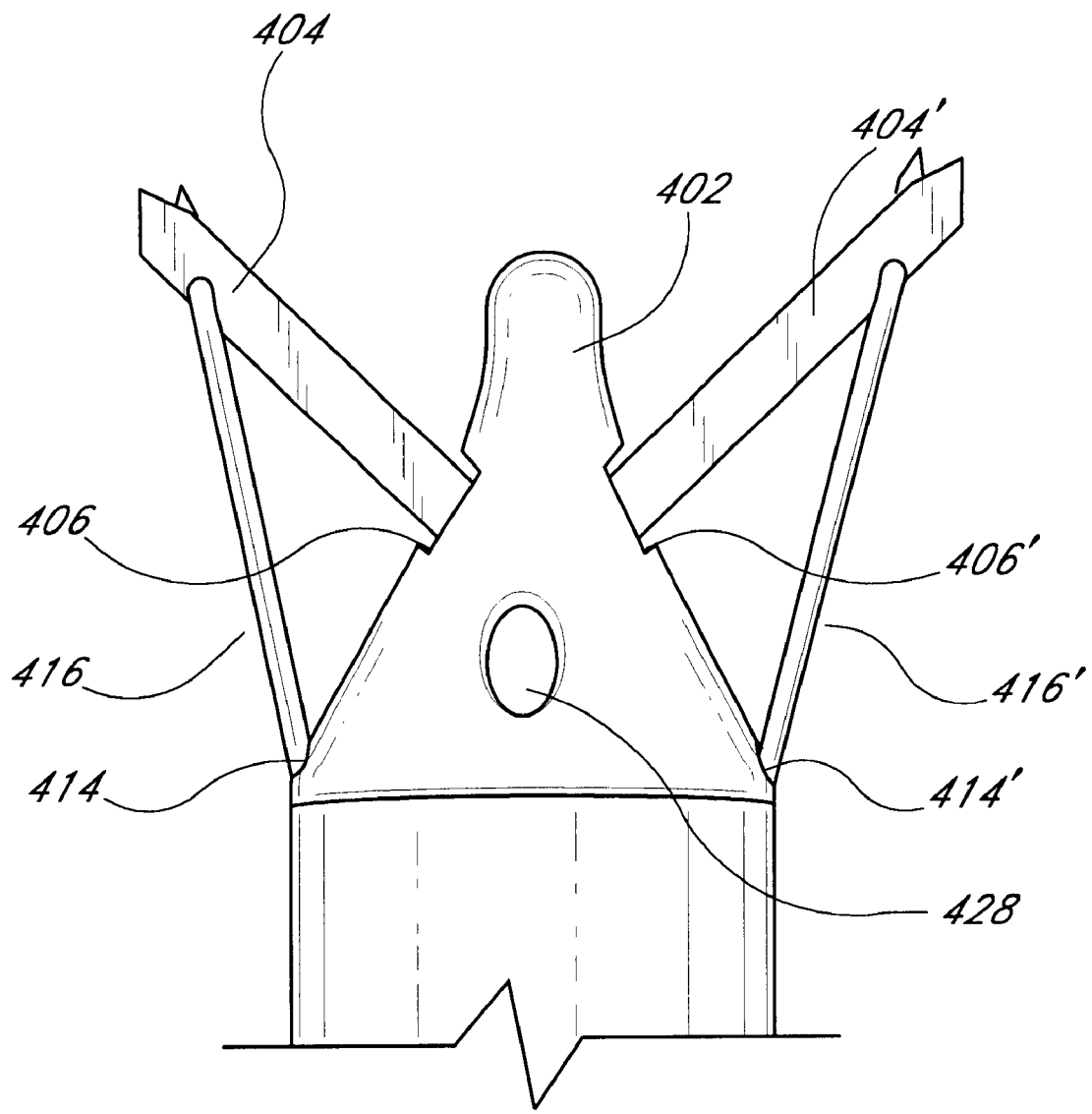
FIG. 18 is a side view of the distal portion of the device of FIG. 17.

FIG. 18 illustrates the distal portion 400 of the suturing device 300 of FIG. 17 in greater detail. The distal portion 400 includes a conically-shaped nose portion 402, a pair of arms 404, 404', a pair of arm apertures 406, 406', a pair of needles 416, 416' and a pair of needle apertures 414, 414'. The nose portion 402 is adapted for insertion into an ostium, infundibulum or similarly shaped structure and provides a means to enable access into narrow passageways or openings. The nose portion may also be used to place the suturing device in optimum position of contact within the surrounding tissue. The arms 404, 404' extend through the arm apertures 406, 406' for penetrating the surrounding tissue in, for example, a conical or funnel-shaped biological structure such as an ostium. The needles 416, 416' extend through the needle apertures 414, 414' for capturing the end portions of the suture from the arms and withdrawing them back toward the device. An opening 428 is provided near or on the nose portion 402 to provide a location for the suture material to extend out of the device 300, as shown in FIG. 20A below.

Figure 19A:
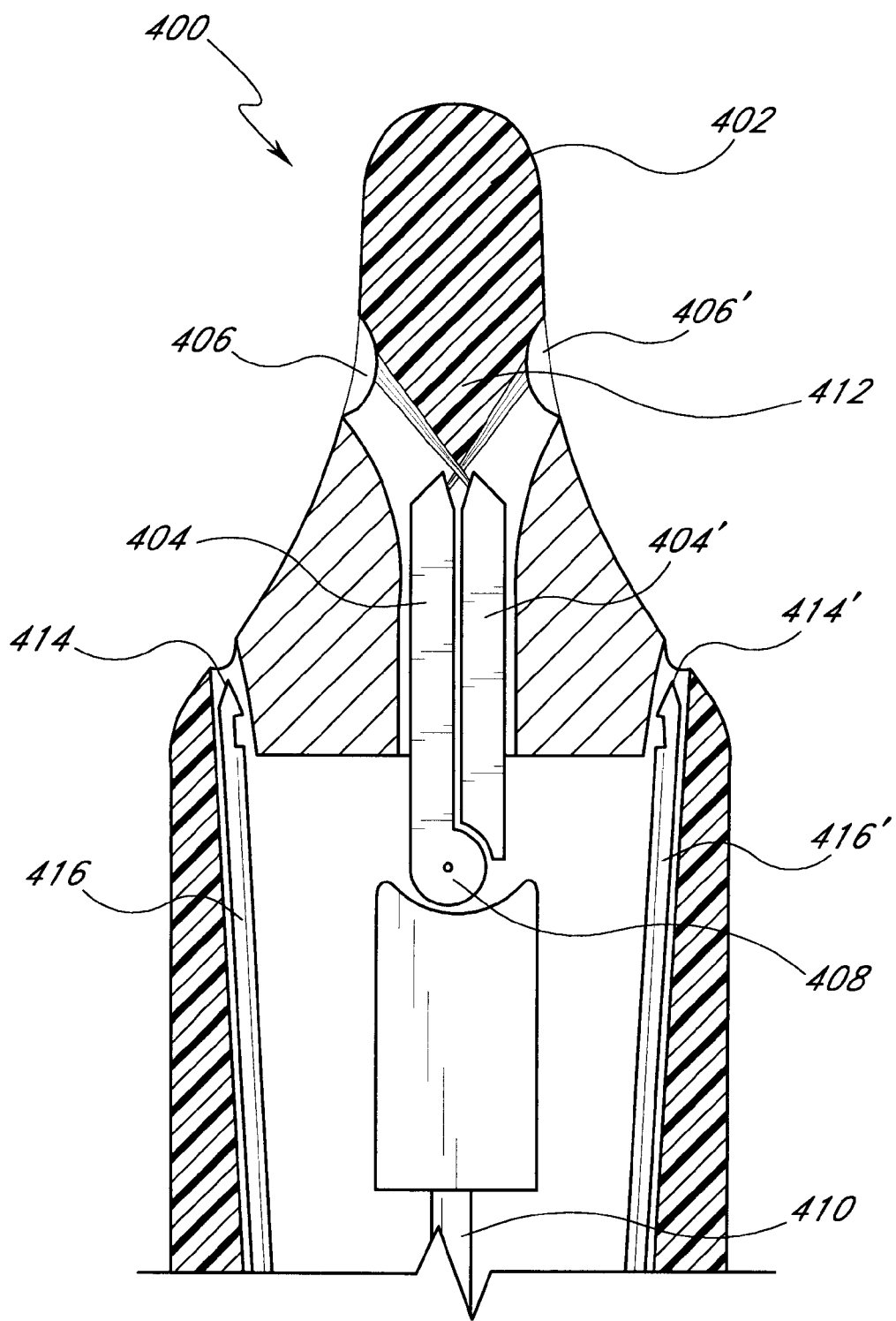
FIGS. 19A–19D are partial cross-sectional views of the distal portion of FIG. 17 as the arms and needles are deployed.
Figure 19B:
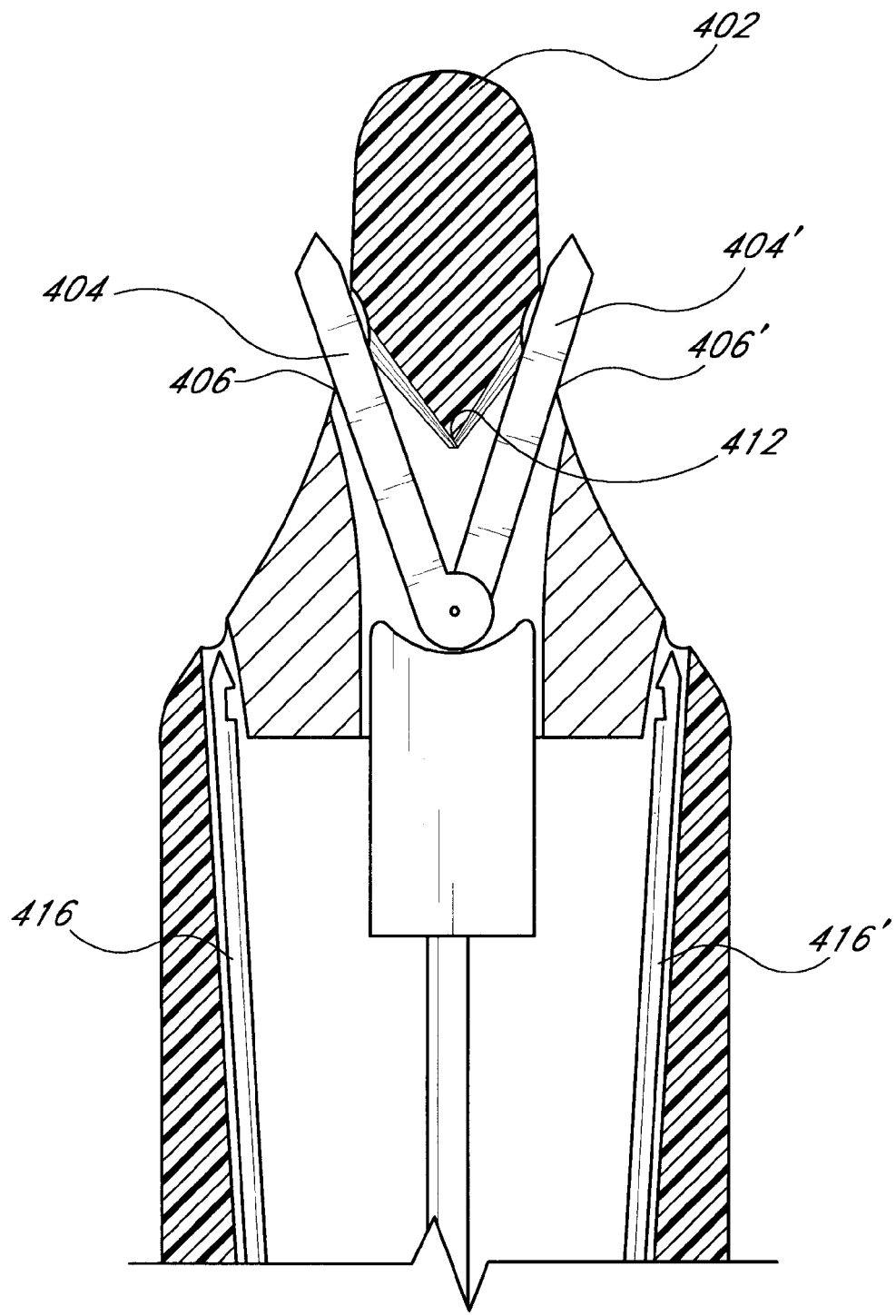
Figure 19C:
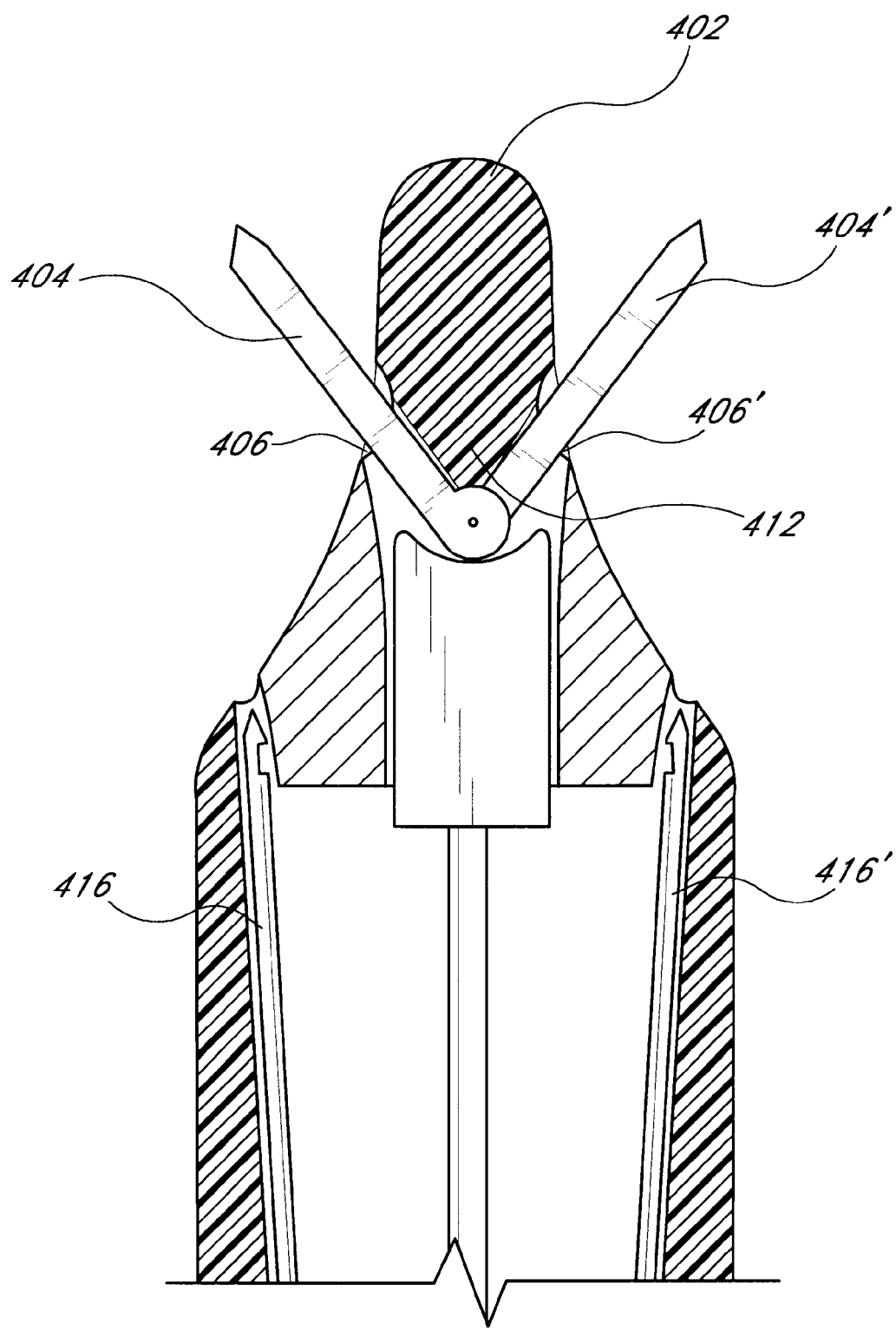
Figure 19D:
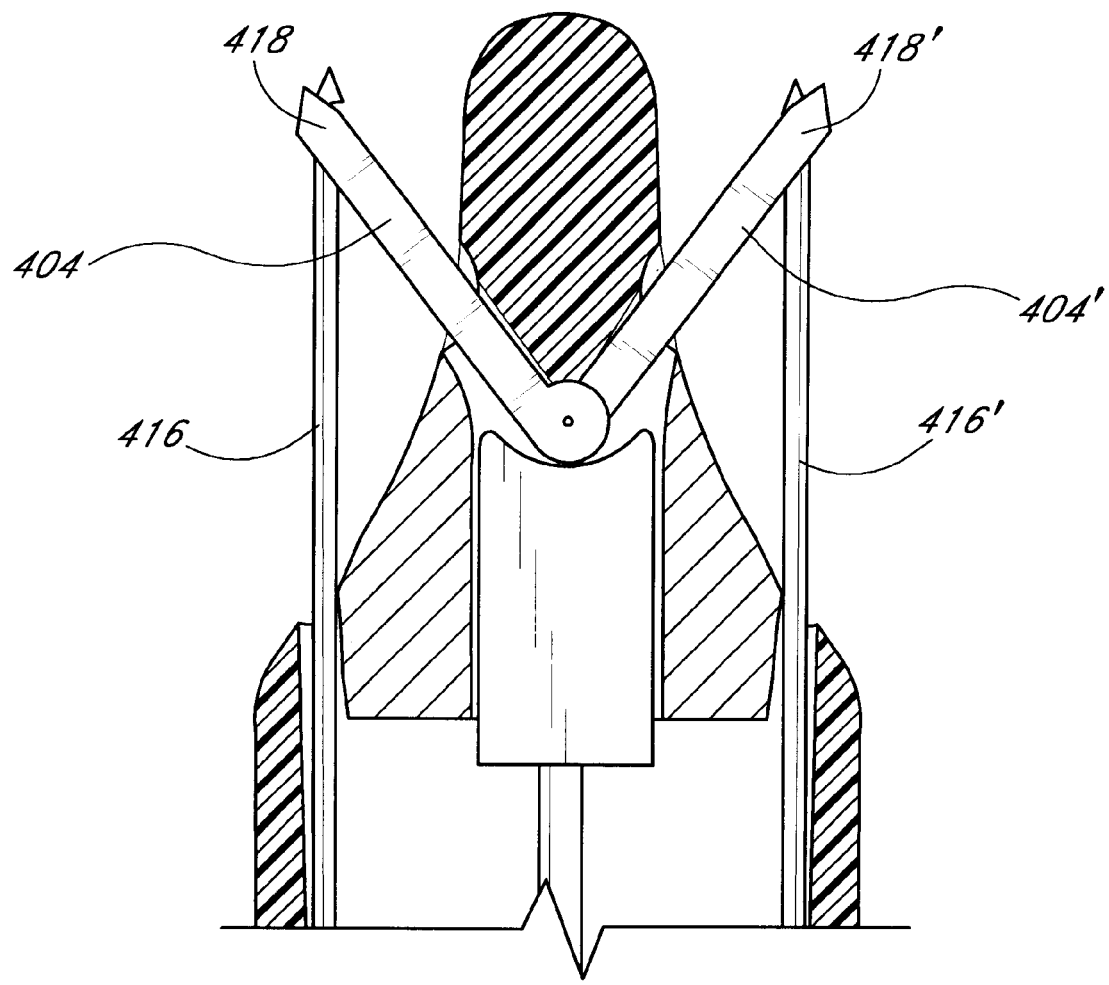

FIGS. 19A–19D sequentially illustrate the movement of the arms and needles of the suturing device shown in FIGS. 17–18. FIG. 19A shows the arms 404, 404' in the recessed position within the apertures 406, 406' in the distal portion 400 of the suturing device. In the recessed position, the arms are fully contained within the suturing device and are configured in a substantially parallel arrangement. The proximal ends of the arms are coupled together by a hinge 408. In FIG. 19B, the arms are shown partially advanced such that the distal end of each arm contacts a spreader mechanism 412 thereby causing the arms 404, 404' to separate. As the arms are extended farther, they are guided outward through the arm apertures 406, 406'. In FIG. 19C, the arms 404, 404' are shown in the fully deployed position, such that each arm extends outward distally and radially away from the distal end of the device. In FIG. 19D, the suturing device is shown with the needles 416, 416' in the extended position, such that the distal end of the needles engage the needle receiving portions 418, 418' of the arms 404, 404'.

A method of using the device of FIG. 17 on a tapered or narrowing body structure, such as the opening of a fallopian tube, is illustrated sequentially in FIGS. 20A through 20F. The physician initially advances the distal portion 400 of the elongated shaft of the suturing device through the patient's body toward the desired body structure 420, such as an ostium. The body structure may be accessed by various methods including: transcervically, transvaginally, percutaneously, laparoscopically, or through an incision in general open surgery. During the insertion of the suturing device, the elongated shaft may be articulated and rotated relative to the main body in order to steer the distal portion through the body structure.

Once the physician places the distal portion 400 of the suturing device at the desired location within the body structure 420, the plunger 306 (shown in FIG. 17) is rotated to advance the arms 404, 404' out of the arm apertures 406, 406' as shown in FIG. 20A. The plunger may be used to advance the arms through a variety of mechanisms. For example, the plunger may be coupled to a threaded screw in the main body and the arms may be coupled to a threaded nut. By rotating the plunger, the nut is advanced or retracted longitudinally along the length of the screw. Further mechanisms for operating the plunger are described in the above-referenced U.S. Pat. No. 6,117,144 and U.S. patent application Ser. No. 09/524,211, filed Mar. 13, 2000, the entirety of which are incorporated by reference. As the arms are advanced outward and become fully deployed, the distal portion of each arm penetrates the tissue of the body structure 420. As the arms penetrate the tissue, the end portions of the suture 422 are inserted into the tissue as shown in FIG. 20B.

After the arms are fully deployed, the physician pushes the plunger distally relative to the main body to advance the needles 416, 416' through the needle apertures and out toward the needle receiving portion of each arm as shown in FIG. 20C. As each needle is advanced, it pierces the tissue of the body structure 420 at a location proximal to the location where the arm pierced the tissue. The needles continue to advance through the tissue until they engage the capture portion 424, 424' (e.g. loops, spheres or ferrules as described above) at the ends of the suture. The needles are then retracted by pulling the plunger proximally relative to the main body thereby removing the suture from the needle receiving portion of each arm and drawing the suture ends back toward the suturing device as shown in FIG. 20D. It should be noted that each suture end portion is inserted into the tissue by an arm along a first path and then retracted from the tissue by a needle along a second path. Therefore, the suture captures a portion of tissue denoted as 426, 426' in FIG. 20D.

After the suture has been applied through the tissue of the biological structure, the arms are retracted by rotation of the plunger in the other direction. The arms are retracted so that the suturing device can be removed from the biological structure without damaging the surrounding tissue. The physician removes the suturing device from the biological structure 420 with the capture portions of the suture ends still held by the needles as shown in FIG. 20E. If necessary, this procedure may be repeated to insert multiple sutures through the walls of the ostium. After the suture(s) are in place, the end portions of each suture are drawn together to create tension and pull the walls of the biological structure into contact with each other as shown in FIG. 20F. The suture ends are secured together with a securement, such as a knot, as described above and to close the biological structure.

The second preferred embodiment described above in FIGS. 17 through 20F advantageously incorporates arms that penetrate the walls of a biological structure at an acute angle relative to the shaft 302. When the arms are in their fully extended position, they form an angle relative to each other that is less than 180°, more preferably, about 90°. The "forward-firing" arms of the second preferred embodiment are particularly advantageous for penetrating ostium-shaped tissue structures. The angle of the arms enables the needles to penetrate deeply into tissue, thereby allowing the suture to grab more tissue and form a stronger connection. The angle also enables the arms to penetrate difficult to reach locations.

Figure 21:
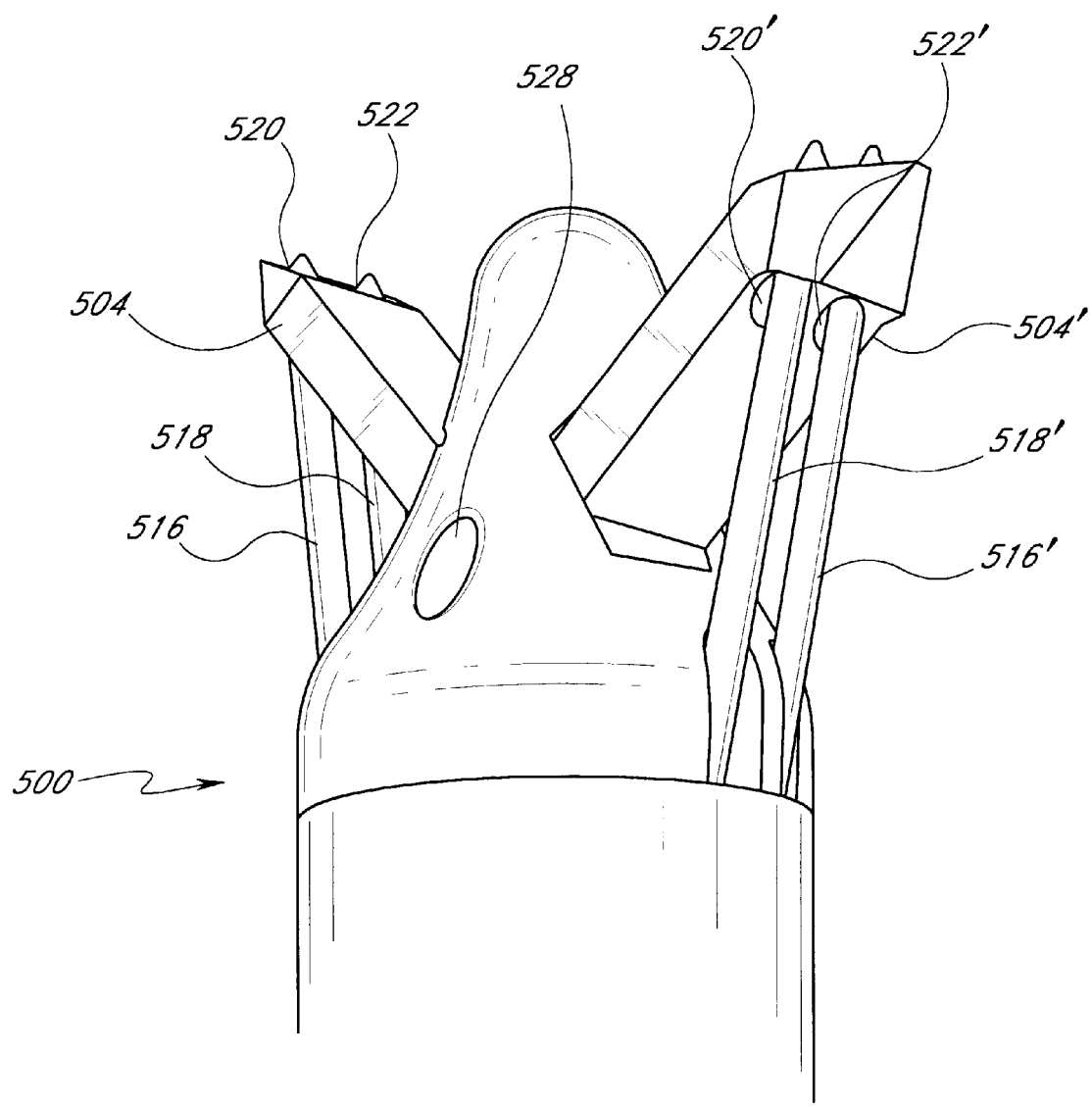
FIG. 21 is a perspective view of the distal portion of another embodiment of a suturing device, wherein the suturing mechanism comprises two arms and two needles per arm in a side-by-side configuration.
Figure 22:
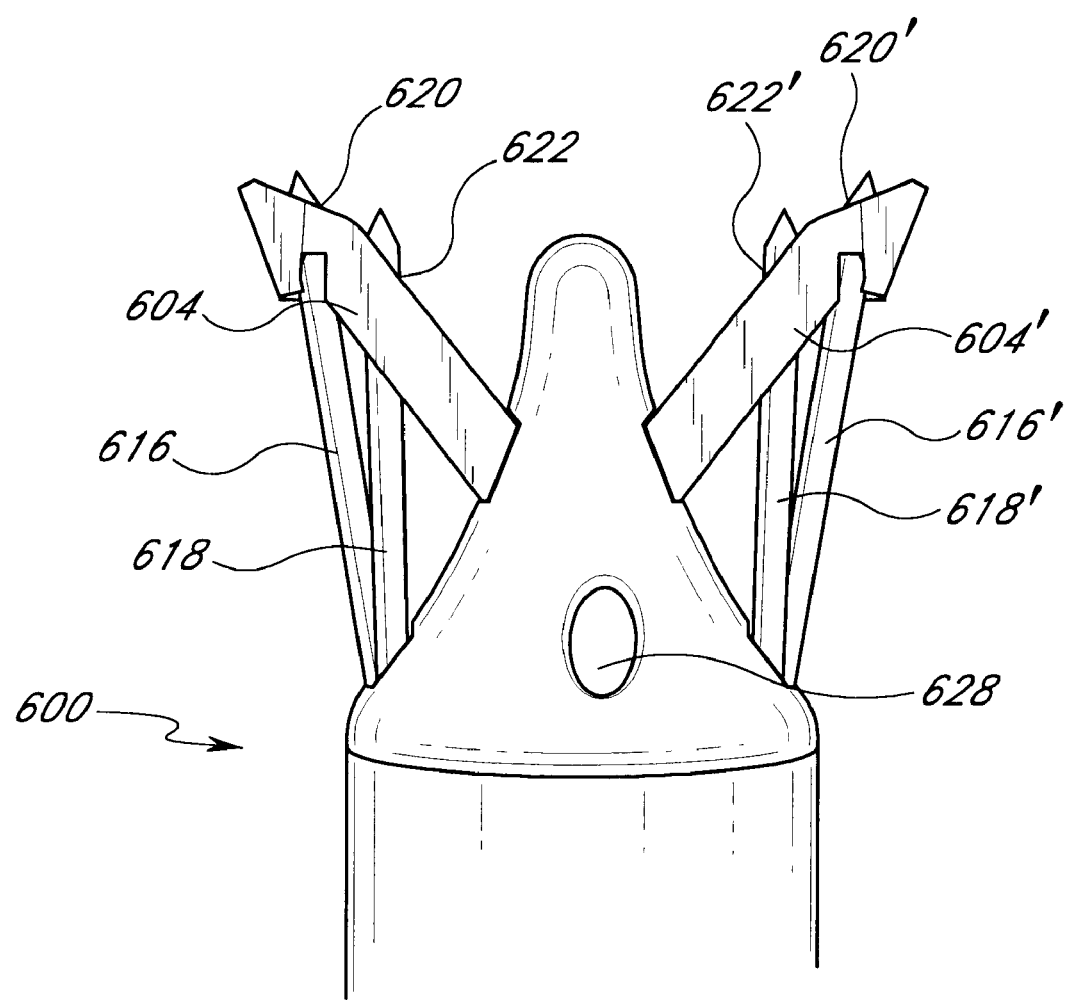
FIG. 22 is a side view of the distal portion of another embodiment of a suturing device, wherein the suturing mechanism comprises two arms and two needles per arm in an inner-outer configuration.
Figure 23:
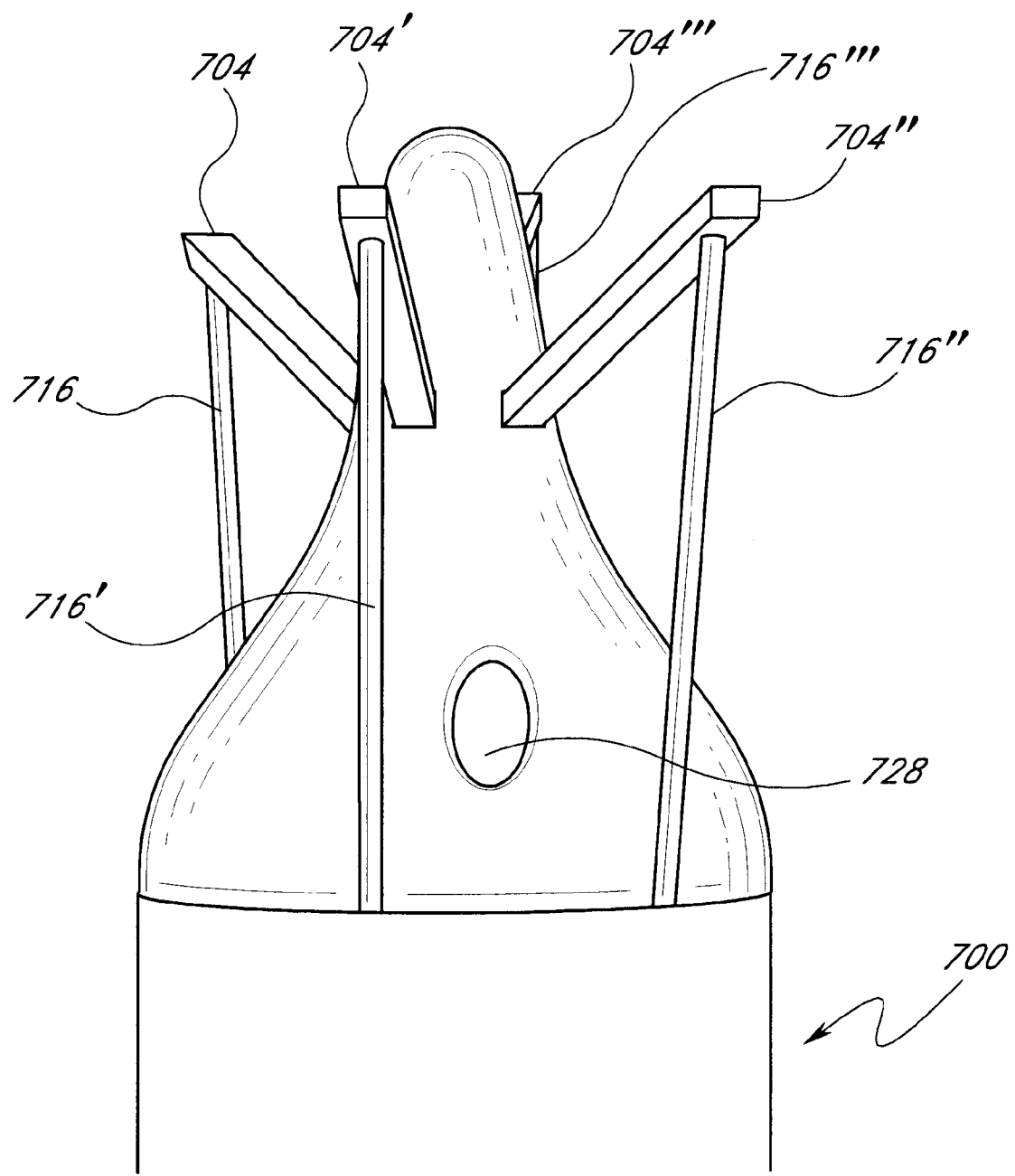
FIG. 23 is a side view of the distal portion of another embodiment of a suturing device, wherein the suturing mechanism comprises four arms and four needles.

FIGS. 21 through 23 show modifications of the second preferred embodiment of the suturing device whereby multiple sutures can be applied simultaneously. FIG. 21 illustrates the distal portion 500 of a suturing device having widened arms 504, 504' that are each formed with two suture end supports 520, 520' and 522, 522' in a side-by-side arrangement. Two pairs of needles 516, 518 and 516', 518' are provided, one pair of needles on each side. On each side, a first needle 516 cooperates with a first end support 520 and a second needle 518 cooperates with a second end support 522. Needles 516 and 516' work together to apply a first suture and needles 518 and 518' work together to apply a second suture. By advancing and retracting both sets of needles at the same time, this embodiment can be used to simultaneously apply two parallel sutures.

FIG. 22 illustrates another modification of the second preferred embodiment in which multiple sutures can be applied simultaneously in a colinear arrangement. The distal portion 600 of a suturing device in accordance with this embodiment includes a pair of arms 604, 604' that are each formed with two suture end supports 620, 622 and 620', 622'. In this modification, the end supports on each arm are arranged such that one of the end supports is distal to the other along the length of the arm. Two needles 616, 618 and 616', 618' are provided on each side arranged in an inner-outer configuration. The first needle 616 advances into the outer suture end support 620 and the second needle 618 advances into the inner suture end support 622. Needles 616 and 616' work together to apply a first suture and needles 618 and 618' work together to apply a second suture. By advancing and retracting both sets of needles at the same time, this embodiment can be used to simultaneously apply two colinear sutures. The colinear sutures are configured with one on top of the other such that a top suture extends into the tissue at locations proximal and distal to the bottom suture.

FIG. 23 illustrates yet another modification to the second preferred embodiment of the suturing device whereby multiple sutures can be applied simultaneously. The distal portion 700 of a suturing device in accordance with this modification comprises four arms 704, 704', 704", 704''' and four needles 716, 716', 716", 716''' equally spaced about the distal portion 700 of the suturing device. This embodiment is designed for simultaneously applying two perpendicular sutures to a conical or funnel-shaped biological structure, such as an ostium. In further modifications, the suturing device can be formed with any even number of arms and needles, such as, for example, six or eight.

Figure 24:
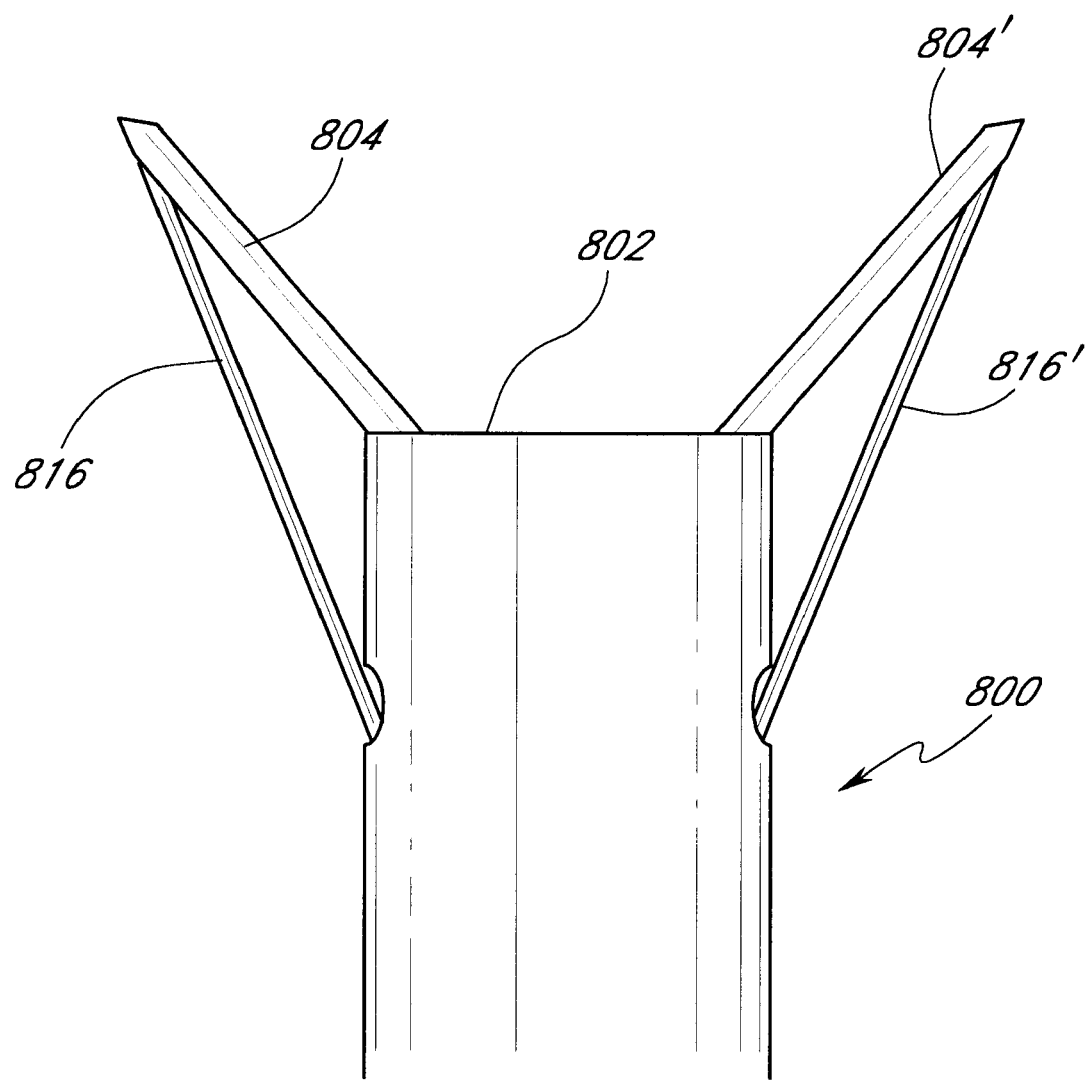
FIG. 24 is a side view of the distal portion of another embodiment of a suturing device, wherein the distal portion of the device is formed with a flat surface.

FIG. 24 illustrates yet another embodiment of a suturing device of the present invention. The distal portion 800 of this suturing device is formed with a flat distal surface 802 such that the arms 804, 804' and needles 816, 816' extend distally beyond the flat distal surface 802 of the elongated shaft when fully deployed. In this embodiment, the suture is provided to the arms through an opening in the distal end of the device. This embodiment may be advantageously used to apply suture to a substantially flat body structure from an external location and is particularly advantageous for closing wounds or surgical incisions.

Figure 25A:
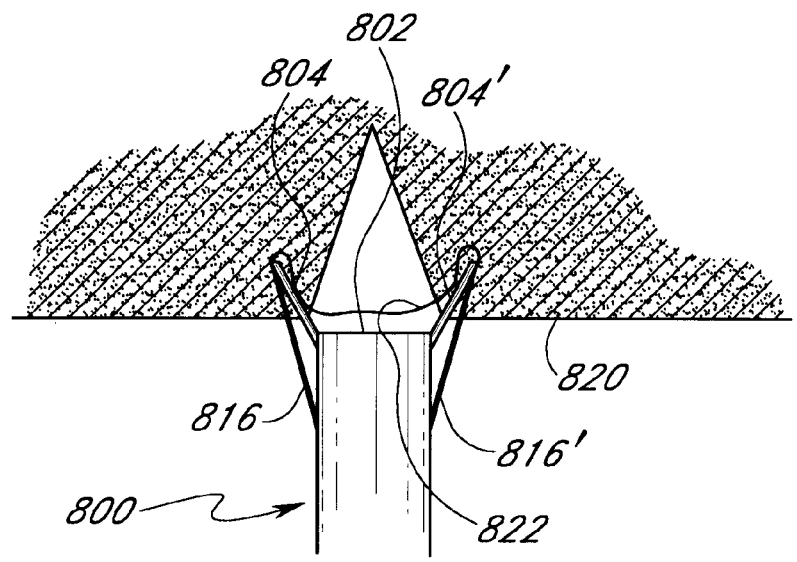
FIGS. 25A–25C are side views of the device of FIG. 24 used to close an incision from an external location, with the incision shown partially cut-away.
Figure 25B:
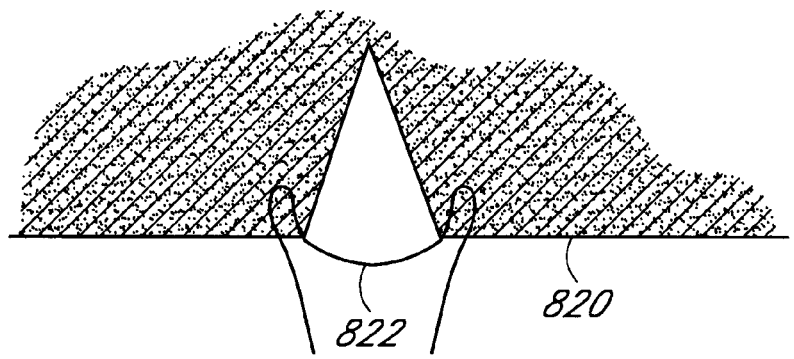
Figure 25C:
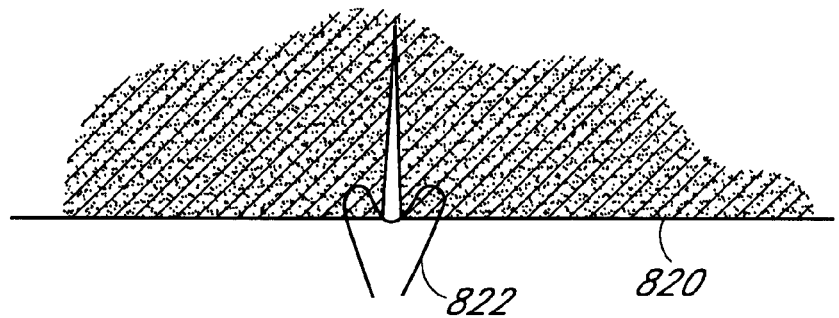

A method of using the device of FIG. 24 for closing an incision in the skin or surface of another biological structure is illustrated sequentially in FIGS. 25A through 25C. As shown in FIG. 25A, the flat distal surface 802 of the suturing device 800 is placed against a substantially flat region of tissue 820 such that the longitudinal axis of the device 800 is substantially perpendicular to the plane of the tissue 820. The plunger mechanism (not shown) is rotated to deploy the arms 804, 804' thereby inserting the end portions of the suture 822 into the tissue 820, one end portion on each side of the incision. The plunger mechanism is then advanced distally to extend the needles 816, 816' into the tissue 820 and capture the end portions of the suture 822. By moving the plunger proximally, the needles are withdrawn thereby pulling the end portions of the suture 822 out of the tissue 820 as shown in FIG. 25B. The end portions of the suture 822 are then pulled to close the incision as shown in FIG. 25C.

It will be appreciated that for each of the embodiments described above, the arms and/or needles can be deployed simultaneously or sequentially. FIGS. 26A and 26B illustrate one embodiment which enables independent deployment of the arms. The suturing device 900 includes, generally, an elongated shaft 902 for insertion into an internal biological structure, a main body 904, two actuation mechanisms 906, 906' and a handle 908 for gripping the suturing device. The actuation mechanisms 906, 906' are located at the proximal end of the main body 904 and are operatively connected to the distal portion 1000 of the suturing device 900. In this modification, each of the arms 1004, 1004' can be actuated independently through independent manipulation of the actuation mechanisms 906, 906'. In such applications, the first needle/arm pair 1004, 1016 would be actuated independently of the second needle arm pair 1004', 1016' (shown in FIG. 27A).

The use of independently deployable arms allows for suturing across large gaps in tissue by first placing a first end of a suture in one area of tissue and then moving the device and placing a second end of the suture in a different area or tissue. In operation, one end of the suture is passed through tissue on one side of a cavity using the first needle arm pair 1004, 1016. The other end of the suture is passed through tissue using the second needle/arm pair 1004', 1016' on the other side of the cavity. This feature may also be advantageous for moving a body structure and attaching it to a new location such as in the treatment of bladder or uterine prolapse.

Figure 27A:
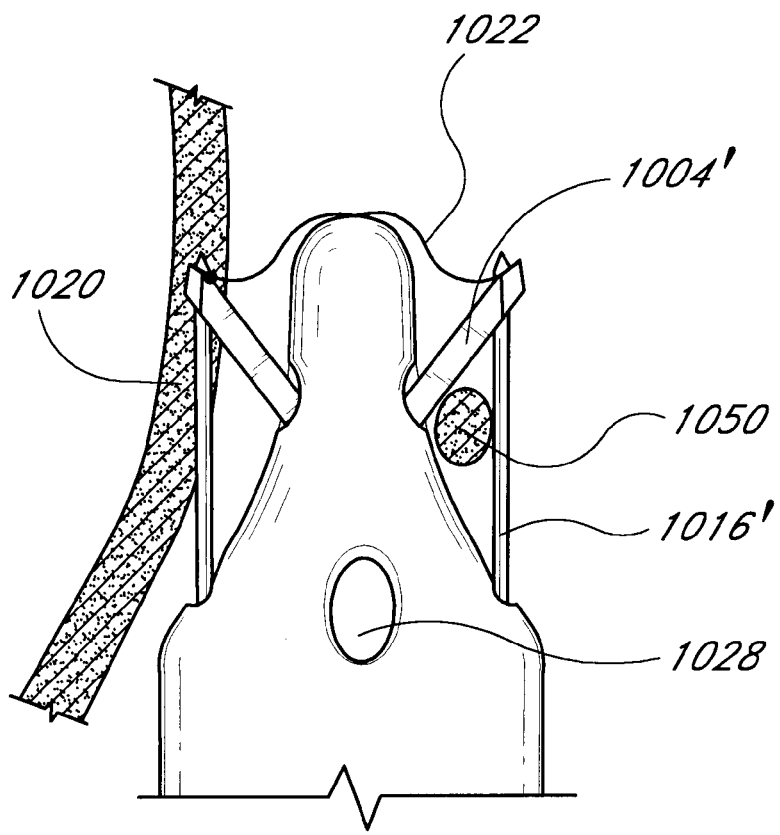
FIG. 27A is a side view of the distal portion of the device of FIG. 26A, shown attaching two biological structures.

Independent actuation of the arms can also be advantageously used to attach or suspend a first body structure to a second body structure. The body structures used in this method can be any implantable or biological structures, including bones, ligaments, muscle tissue and body organs. In operation, one end of a suture is looped around a first body structure 1050 for use as an anchor as illustrated in FIG. 27A. One of the arms 1004' is deployed on one side of the body structure 1050 and the corresponding needle 1016' is deployed on the other side of the first body structure, such that the arm 1004', the needle 1016' and the elongated body surround the body structure. One end portion of the suture 1022 is passed from the arm 1004' to the needle 1016' to form a loop around the first body structure.

Figure 27B:
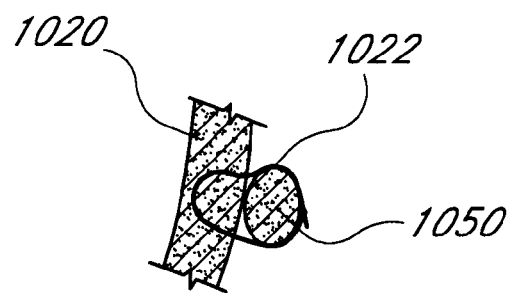
FIG. 27B is a cross-sectional view of the biological structures of FIG. 27A attached together.

The other end portion of the suture can then be threaded through a second body structure or tissue 1020 that is adjacent to, or distanced from, the first body structure. A penetrating arm 1004 penetrates the tissue 1020, and a deploying needle 1016 is moved relative to the arm 1004 to retrieve the suture end held in the arm 1004. Alternatively, the second arm and needle can be used to loop a suture around a second body structure, as with the first arm and needle. The ends of the suture 1022 are then pulled tight to bring the body structure 1050 and the tissue 1020 together as illustrated in FIG. 27B.

It will be appreciated that the arms 1004 and 1004' can be deployed in any preferred sequence, and thus, arm 1004 can be used to penetrate tissue before arm 1004' is used to loop a body structure. It will also be appreciated that the arms 1004 and 1004' can be deployed simultaneously. In one embodiment of the device of FIG. 27A, the arm 1004' that is positioned around the body structure has a blunt tip, while the arm 1004 that penetrates tissue has a sharp tip.

The embodiment of FIG. 27A may also be used for suspending an organ from an adjacent or distant body structure, such as, for example, in the treatment of bladder or uterine prolapse. Organ suspension may be accomplished with this embodiment by penetrating an arm and firing an needle into an organ to place a first end of a suture, moving the suturing device to traverse a space, and then positioning a second arm and firing a second needle around a ligament to loop the second end of the suture around the ligament. By tightening the suture, the organ is suspended by using the ligament.

The ability of the suturing device to loop suture around a body structure may also be advantageously applied to an improved method for performing male sterilization. The vas deferens are first accessed using either a conventional approach (through scrotal incisions) or through a tiny puncture (similar to the no-scalpel vasectomy approach). After accessing the vas deferens, one arm of the suturing device is then deployed on one side of the vas deferens and one needle is deployed on the other side. The needle picks up the suture to loop suture around the vas deferens. The suture is then pulled tight and tied off to block the lumen in the vas deferens thereby blocking the flow of sperm into the ejaculatory ducts.

Other devices, including those described above, may also be used for looping suture around a body structure or for suspending a first body structure to a second body structure. For example, suturing devices may be used in which the arms are not moveable from within the elongated body to outside the elongated body. Rather, in these embodiments, the arm or arms may be fixed relative to the elongated body, and may simply be placed around the body structure to be suspended before the needles are deployed. Furthermore, once a first body structure is suspended to a second body structure, it will be appreciated that the distance between the two structures can be adjustable using an adjustment feature, such as a turnbuckle, that can be utilized to draw up an organ, or draw to an organ.

It will also be appreciated that a suturing device with one or more fixed arms extending from the elongated body can be used in other applications as well. For example, this device can be used to place suture into tissue simply by manipulating the device such that the arm or arms punctures the desired tissue location. The needles then deploy in the manner described above to grab the suture ends mounted on the arms of the device.

Figure 28B:
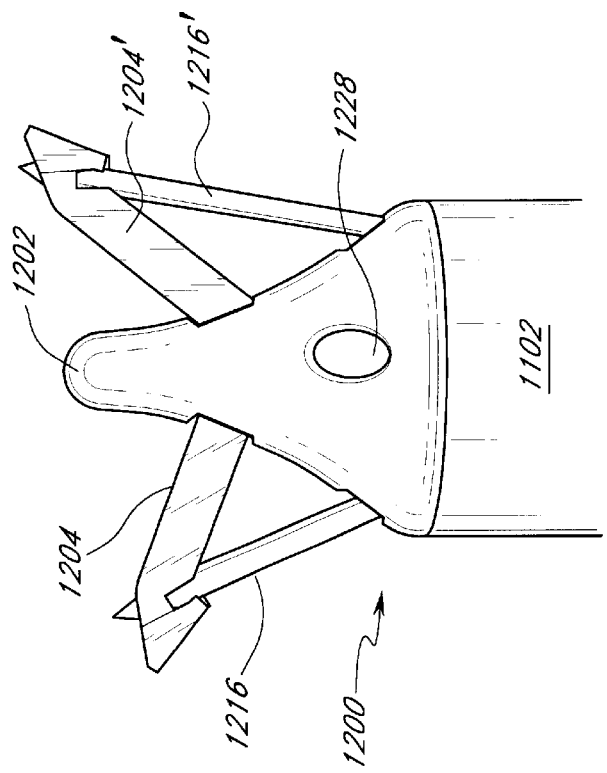
FIG. 28B is a side view of the distal portion of the device of FIG. 28A.
Figure 28A:
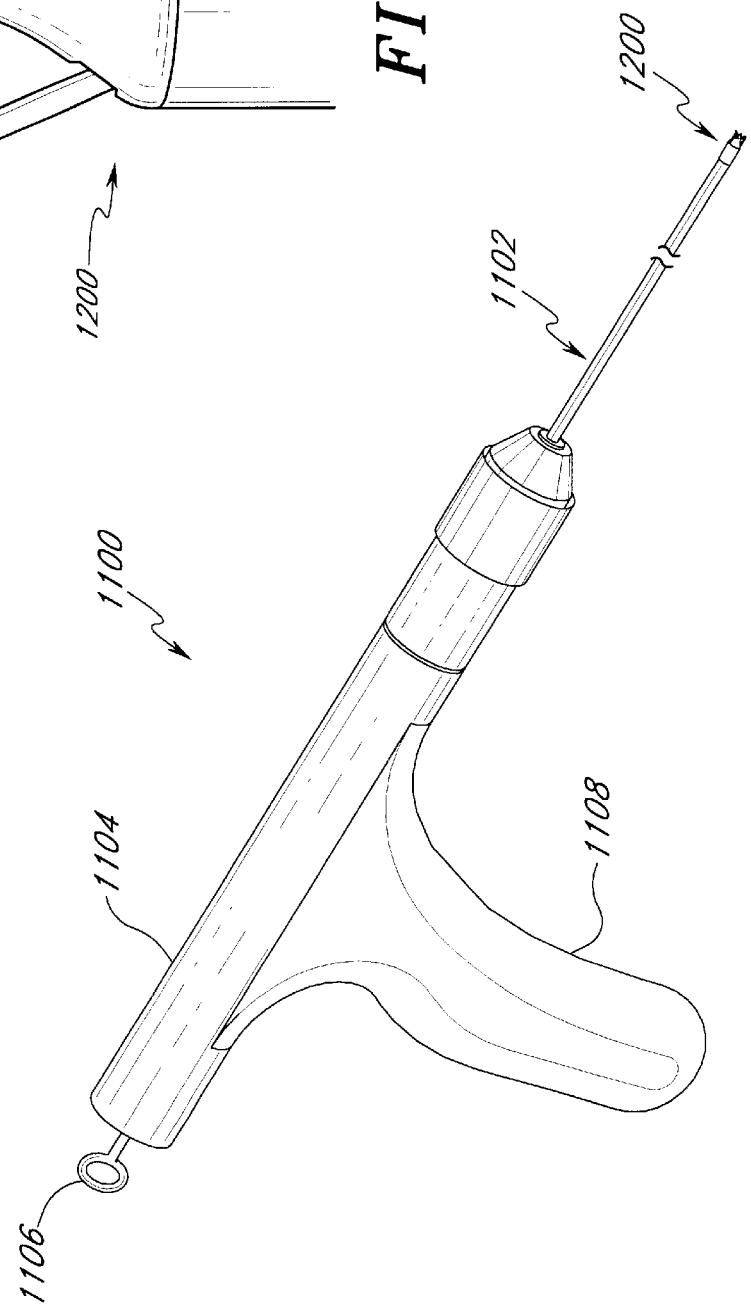
FIG. 28A is a perspective view of another embodiment of a suturing device, wherein the arms and needles can be deployed asymmetrically.

FIGS. 28A and 28B illustrate yet another embodiment of a suturing device of the present invention. The suturing device 1100 includes, generally, an elongated shaft 1102 for insertion into an internal biological structure, a main body 1104, a plunger 1106 and a handle 1108 for gripping the suturing device. The plunger 1106 is located at the proximal end of the main body 1104 and is operatively connected to the distal portion 1200 of the suturing device 1100. In this modification, the arms 1204, 1204' are simultaneously deployed into an asymmetrical configuration using a single plunger 1106. This modification can be advantageously used to simultaneously penetrate different types of tissue that require different angles of entry or different tissue capture geometries. This modification can also be used for surrounding a body structure with a first arm/needle pair and applying suture through tissue with the other arm/needle pair. With this embodiment, the needle 1216, 1216' have trajectories that are preferably adjusted to find the proper placement in the arms 1204, 1204'. This embodiment can also be combined with independent arm actuation, as described above with reference to FIGS. 26A–27B, thereby providing independent arm actuation and asymmetric arm deployment in the same unit.

In variations of the preferred embodiments described above, each of the suturing devices described above may be formed with a guidewire lumen extending lengthwise through the elongated body for slidably receiving a guidewire. Such a lumen preferably terminates at an opening located on the distal portion of the device. Such an opening may be similar to the opening 428 shown in FIG. 18. The suturing device may be advanced over the guidewire to facilitate the placement of the device in the patient's body. In other variations, each of the suturing devices described above may be formed with an additional lumen for receiving an endoscope for viewing the target site within the body.

In another aspect of the present invention, various devices and methods are provided for performing a hysterectomy. In a first preferred method for performing a hysterectomy, a suturing device is inserted into each fallopian tube as described above and suture is applied to each fallopian tube to close the lumen. A cutting tool is then inserted into each fallopian tube and each fallopian tube is severed thereby disconnecting the tubes from the uterus. After the fallopian tubes have been severed, the uterus is inverted through the cervix. The uterus is cut away from the cervix and is removed from the body. A suturing device as described above can then be used to apply suture to the cervix to close the distal portion of the vagina. For closure of the cervix, it may be preferable to use a suturing device with multiple arms and needles, for example, 6 or 8.

In a second method for performing a hysterectomy, a suturing device is inserted into each fallopian tube as described above and suture is applied to each fallopian tube to close the lumen. A cutting tool is then inserted into each fallopian tube and each fallopian tube is severed thereby disconnecting the tubes from the uterus. After the fallopian tubes have been severed, the uterus is cut away from the cervix and is removed from the body. A suturing device as described above is then used to apply suture to the cervix to close the distal portion of the vagina.

In a third preferred method for performing a hysterectomy, a suturing device is inserted into each fallopian tube as described above and suture is applied to each fallopian tube to close the lumen. A cutting tool is then inserted into each fallopian tube and each fallopian tube is severed thereby disconnecting the tubes from the uterus. After the fallopian tubes have been severed, a suturing device such as described is inserted into the cervical opening, and suture ends are placed loosely applied around the opening of the cervix in a purse-string arrangement. The uterus is cut around the cervix at a location distal to the placed sutures and is removed from the body. The ends of the sutures are then pulled together and tied to close the distal portion of the vagina.

In a fourth preferred method for performing a hysterectomy, a suturing device is inserted into each fallopian tube as described above and suture is applied to each fallopian tube to close the lumen. A cutting tool is then inserted into each fallopian tube and each fallopian tube is severed thereby disconnecting the tubes from the uterus. After the fallopian tubes have been severed, suture is loosely applied around the cervical opening as described in the third method above. After the suture has been applied, the uterus is inverted through the cervix. The uterus is then cut at a location distal of the placed sutures and the uterus is removed from the body. The ends of the sutures are then pulled together and tied to close the distal portion of the vagina.

While embodiments and applications of this invention have been shown and described, it will be apparent to those skilled in the art that various modifications are possible without departing from the scope of the invention. It is, therefore, to be understood that within the scope of the appended claims, this invention may be practiced otherwise than as specifically described.

What is claimed is:

1. A suturing device for applying a suture, comprising:
   an elongated body;
   at least one arm having a suture mounting portion to releasably hold a portion of said suture, said arm being mounted to cause an end portion of said arm to move (i) away from said elongated body from a first position to a second position and (ii) towards said elongated body from the second position to the first position, said end portion of said arm being adapted to penetrate tissue as the arm moves away from said elongated body to said second portion while holding said portion of the suture during such movement; and
   at least one needle having a distal end, said needle mounted to move relative to said elongated body, said distal end of said needle movable from a first position adjacent to said elongated body to a second position adjacent said suture mounting portion of said arm when said arm is in said second position;
   wherein said distal end of said needle is adapted to capture said portion of the suture from the suture mounting portion of the arm and draws said portion of said suture toward said elongated body.

2. The suturing device of claim 1, wherein said second position of said needle is spaced away from said elongated body.

3. The suturing device of claim 1, wherein the arm is hingedly mounted to an actuating rod, said actuating rod being movable within a lumen of the elongated body.

4. The suturing device of claim 1, wherein the end portion of the arm includes a pointed tip.

5. The suturing device of claim 1, comprising:
   first and second arms each having a suture mounting portion to releasably hold an end portion of a suture; and
   first and second needles adapted to capture the end portions of the suture from the suture mounting portions of the first and second arms and draw the end portions of the suture proximally.

6. The suturing device of claim 5, wherein the first and second arms when in their second position are substantially parallel to one another.

7. The suturing device of claim 5, wherein the first and second arms when in their second position form an angle that is less than 180 degrees.

8. The suturing device of claim 5, wherein the first and second arms each have two suture mounting portions.

9. The suturing device of claim 8, wherein the two suture mounting portions on each arm are side-by-side.

10. The suturing device of claim 8, wherein one of the two suture mounting portions on each arm is distal to the other.

11. The suturing device of claim 5, wherein the first and second arms are separately moveable.

12. The suturing device of claim 5, wherein the first and second needles are separately moveable.

13. The suturing device of claim 1, wherein the end portions of the suture are loops.

14. The suturing device of claim 1, wherein the end portions of the suture are substantially spherical in shape.

15. The suturing device of claim 1, wherein the end portions of the suture comprise a ferrule.

16. The suturing device of claim 1, wherein the end portion of the at least one arm, when the arm is in its second position, is distal to a distal end of the elongated body.

17. A suturing device for applying a suture, comprising:
    an elongated body;
    at least one arm connected to said elongated body having a suture mounting portion and an end portion, said suture mounting portion being formed to releasably hold an end portion of said suture, said end portion of said arm being adapted to penetrate tissue; and
    at least one needle having a distal end, said needle being extendable and retractable relative to said elongated body, said distal end of said needle being adapted for cooperation with said suture mounting portion of said arm;
    whereby said needle can be extended such that said distal end of said needle captures said end portion of said suture from said suture mounting portion of said arm and said needle can be retracted to draw said end portion of said suture back toward said elongated body.

18. The suturing device of claim 17, wherein said arm is capable of being advanced and retracted from said elongated body.

19. The suturing device of claim 18, wherein said arm further comprises a proximal end, said proximal end of said arm being coupled to an actuating rod, said actuating rod being movable within a lumen of the elongated body to advance and retract said arm.

20. A suturing device for applying a suture, comprising:
    an elongated body;
    two arms located on opposite sides of said elongated body, each of said arms having a suture mounting portion and an end portion, said suture mounting portions being formed to releasably hold an end portion of said suture, said arms being extendable and retractable relative to said elongated body, said arms having sharp end portions adapted to penetrate tissue when said arms are extended; and
    two needles located on opposite sides of said elongated body, each needle having a distal end, said needles being extendable and retractable relative to said elongated body, said distal ends of said needles being adapted for cooperation with said suture mounting portions of said arms when said needles and said arms are extended;
    whereby said arms are advanced outward from said elongated body, said needles are advanced distally from said elongated body such that said distal ends of said needles engage and capture said end portions of said sutures from said suture mounting portions of said arms, and said needles are retracted to draw said end portions of said sutures back toward said elongated body.

* * * * *

UNITED STATES PATENT AND TRADEMARK OFFICE
CERTIFICATE OF CORRECTION

PATENT NO. : 6,911,034 B2
APPLICATION NO. : 09/882821
DATED : June 28, 2005
INVENTOR(S) : Anthony Nobles et al.

It is certified that error appears in the above-identified patent and that said Letters Patent is hereby corrected as shown below:

Column 17,
Line 24, after "second" delete "portion" and insert -- position --.

Signed and Sealed this

Twentieth Day of June, 2006

JON W. DUDAS
*Director of the United States Patent and Trademark Office*